United States Patent
Axelson et al.

(10) Patent No.: US 12,133,653 B2
(45) Date of Patent: Nov. 5, 2024

(54) PARTIAL KNEE IMPLANTS AND METHODS FOR INSTALLING THE SAME

(71) Applicant: Encore Medical, L.P., Austin, TX (US)

(72) Inventors: Stuart L. Axelson, Succasunna, NJ (US); Vasily Romanov, Jersey City, NJ (US); Rachel Patel, Austin, TX (US); Anthony J. La Rosa, Wharton, NJ (US); Robert Michael Meneghini, McCordsville, IN (US); Scott Sporer, Wheaton, IL (US); Michael Taunton, Rochester, MN (US); James Browne, Charlottesville, VA (US); Raymond Kim, Vail, CO (US); Joseph Jankiewicz, Coronado, CA (US); Mark McBride, Coronado, CA (US); Brian T. Palumbo, Tampa, FL (US); Michael Patrick Bradley, Wakefield, RI (US)

(73) Assignee: ENCORE MEDICAL, L.P., Austin, TX (US)

( * ) Notice: Subject to any disclaimer, the term of this patent is extended or adjusted under 35 U.S.C. 154(b) by 293 days.

(21) Appl. No.: 17/164,520

(22) Filed: Feb. 1, 2021

(65) Prior Publication Data
US 2021/0236142 A1 Aug. 5, 2021

Related U.S. Application Data

(60) Provisional application No. 62/706,370, filed on Aug. 12, 2020, provisional application No. 62/970,621, filed on Feb. 5, 2020.

(51) Int. Cl.
*A61B 17/15* (2006.01)
*A61B 17/17* (2006.01)
(Continued)

(52) U.S. Cl.
CPC ........ *A61B 17/155* (2013.01); *A61B 17/1764* (2013.01); *A61F 2/3859* (2013.01);
(Continued)

(58) Field of Classification Search
CPC .............. A61B 17/155; A61B 17/1675; A61B 17/1764; A61F 2/38; A61F 2/3859; A61F 2/461; A61F 2/4684; A61F 2002/3895
See application file for complete search history.

(56) References Cited

U.S. PATENT DOCUMENTS

2004/0153089 A1 8/2004 Sanford
2006/0217734 A1 9/2006 Sanford
(Continued)

FOREIGN PATENT DOCUMENTS

WO WO 2017/007820 A1 1/2017
WO WO-2020000030 A1 * 1/2020 ........... A61B 17/025

OTHER PUBLICATIONS

International Search Report and Written Opinion in International Application No. PCT/US2021/016082, mailed Jul. 5, 2021 (17 pages).

*Primary Examiner* — Samuel S Hanna
(74) *Attorney, Agent, or Firm* — Nixon Peabody LLP

(57) ABSTRACT

The present disclosure is a femoral preparation guide and a kit of surgical components related to the femoral preparation guide. The femoral preparation guide is for use on a condyle of a femur during a surgical procedure in which the condyle receives a femoral condylar implant. The femoral preparation guide includes a posterior portion for fitting over a posterior region of the condyle and a distal portion for fitting over a distal region of the condyle. The distal portion is at an angle relative to the posterior portion. The distal portion includes first and second resections slots for receiving cutting tools that provide two resections of the condyle. The
(Continued)

first and second resections slots being at angles relative to each other.

15 Claims, 20 Drawing Sheets

(51) Int. Cl.
*A61F 2/38* (2006.01)
*A61F 2/46* (2006.01)

(52) U.S. Cl.
CPC ............ *A61F 2/3868* (2013.01); *A61F 2/461* (2013.01); *A61F 2002/4681* (2013.01)

(56) References Cited

U.S. PATENT DOCUMENTS

| | | |
|---|---|---|
| 2008/0058949 A1 | 3/2008 | Dees |
| 2017/0007273 A1* | 1/2017 | Freiberg ............. A61B 17/1764 |
| 2018/0103966 A1 | 4/2018 | Jones |
| 2021/0267607 A1* | 9/2021 | Miles ................... A61B 17/157 |
| 2022/0287724 A1* | 9/2022 | Yeager ............... A61B 17/1764 |

* cited by examiner

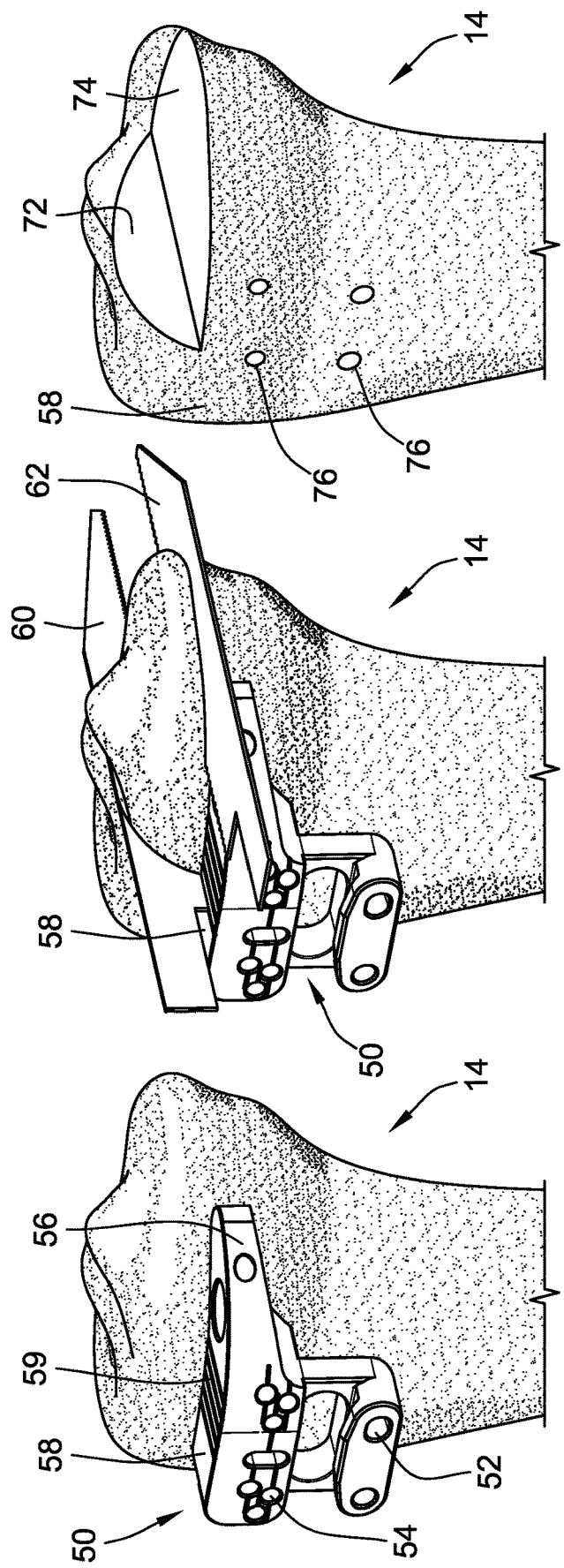

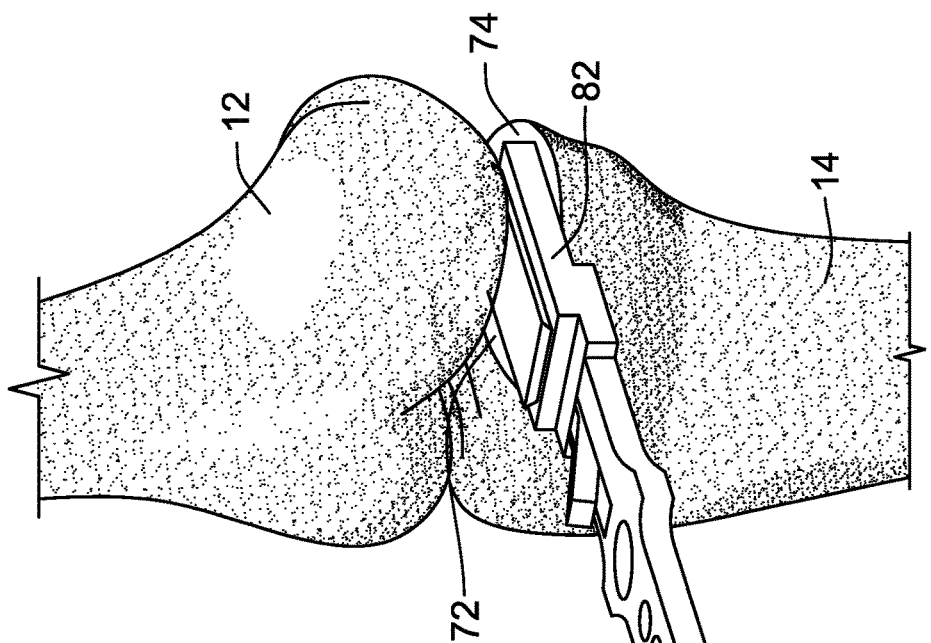
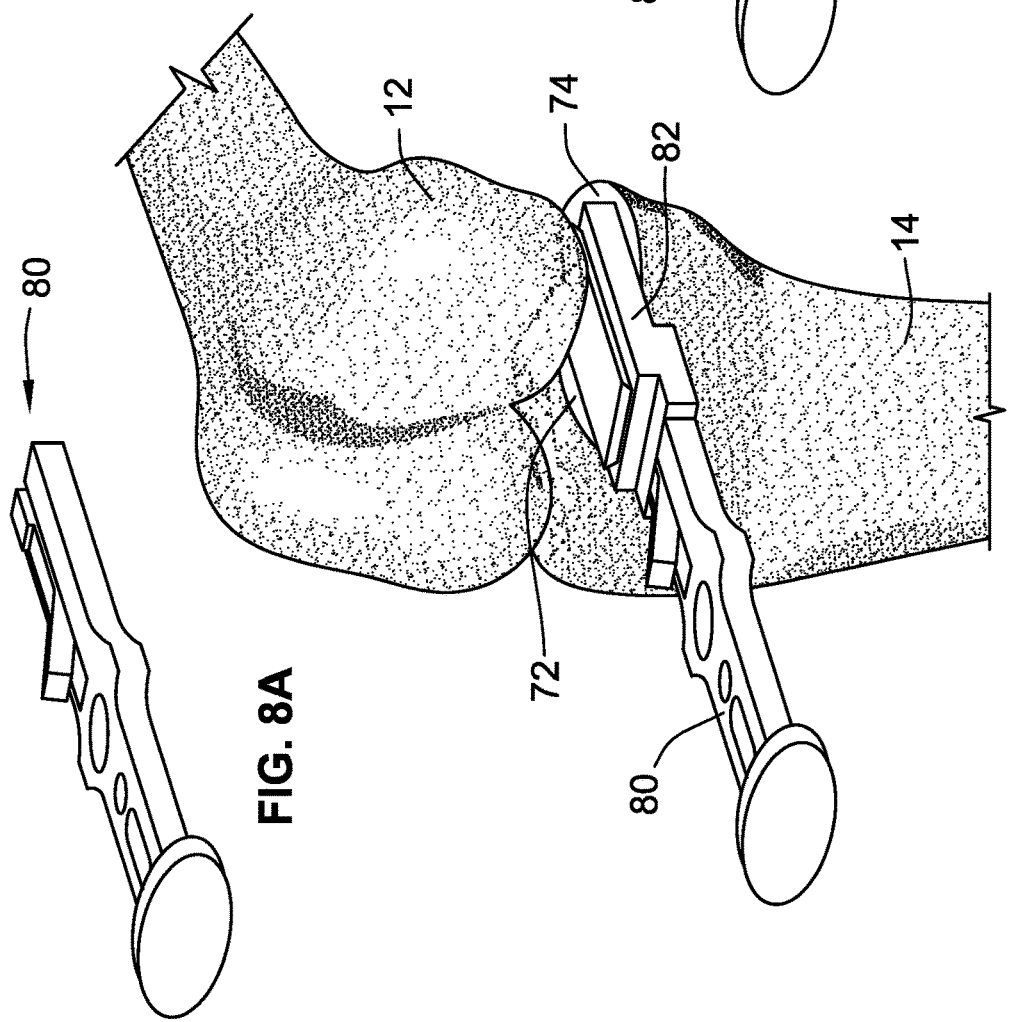

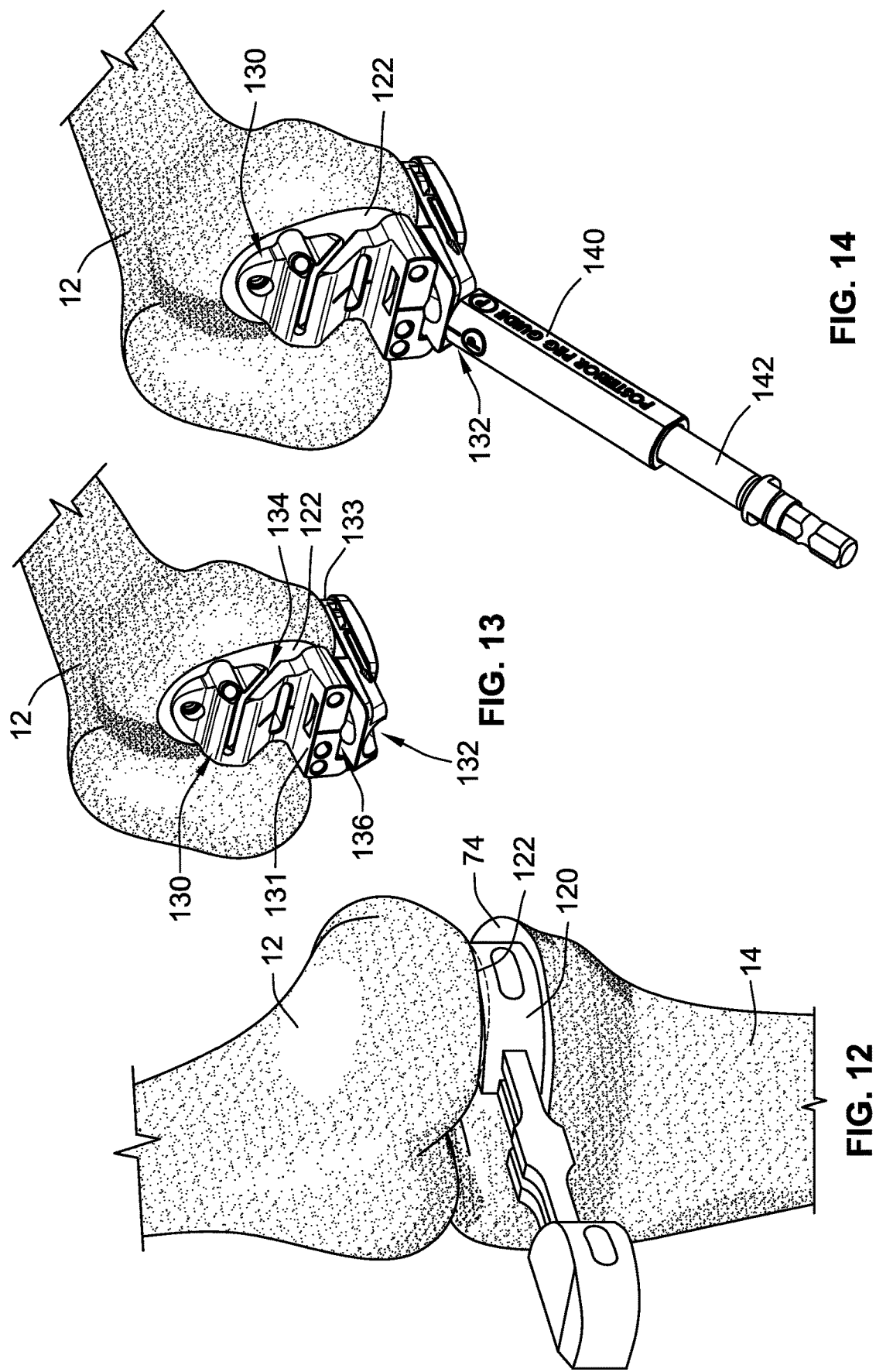

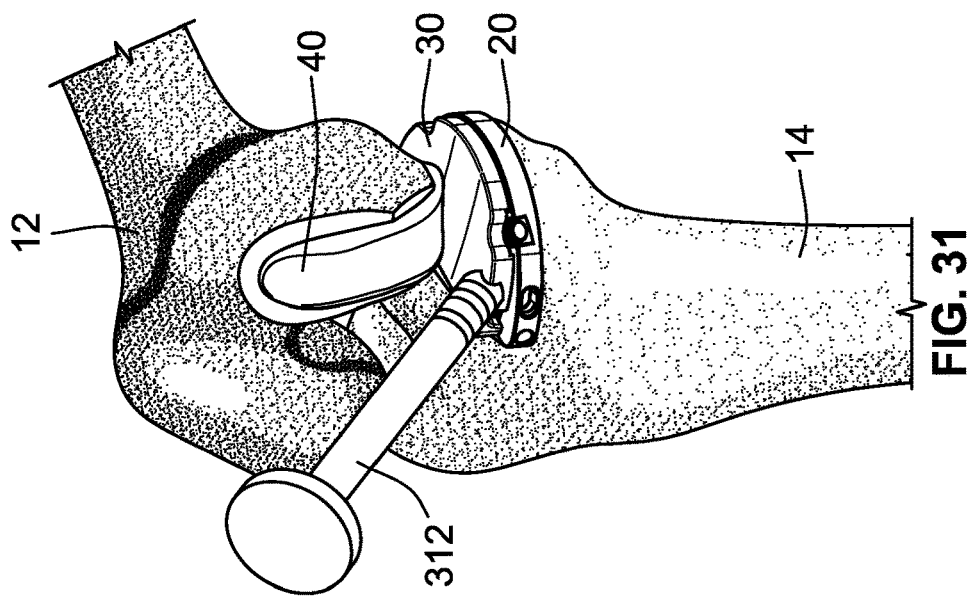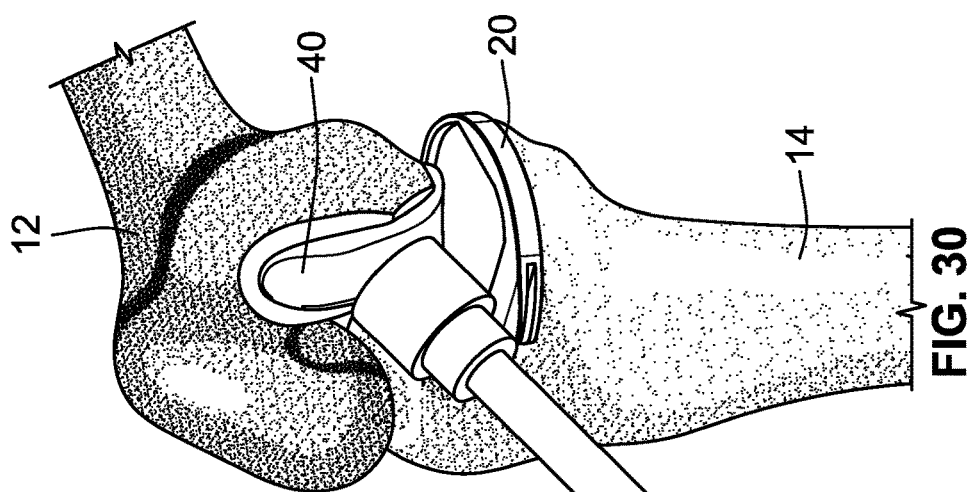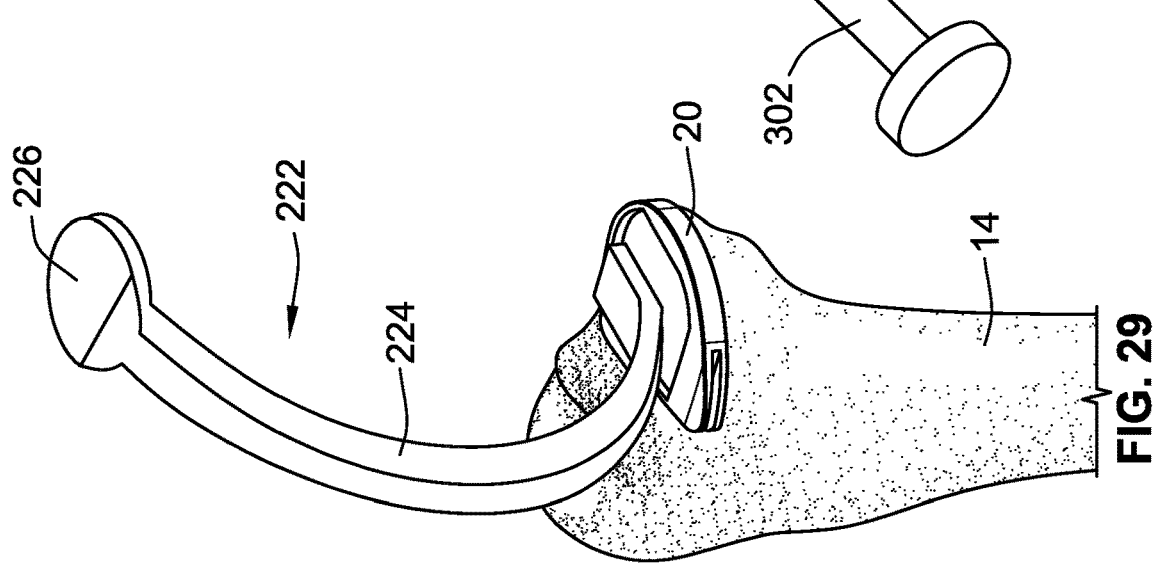

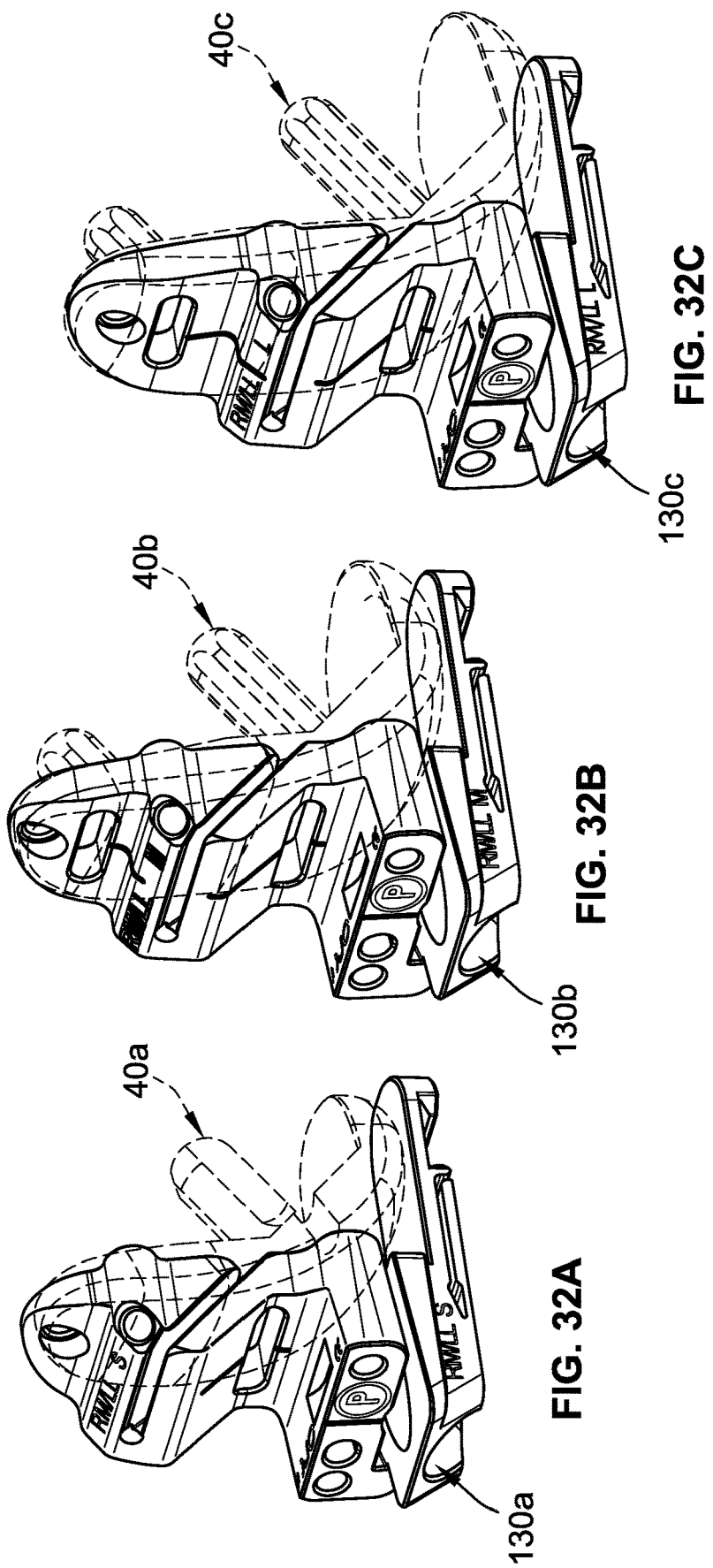

PARTIAL KNEE IMPLANTS AND METHODS FOR INSTALLING THE SAME

RELATED APPLICATION

This application claims the benefit of, and priority to, U.S. Provisional Application No. 62/970,621, filed on Feb. 5, 2020, and U.S. Provisional Application No. 62/706,370, filed on Aug. 12, 2020, each of which is hereby incorporated by reference in its entirety.

TECHNICAL FIELD

The present disclosure relates to implants and surgical methods, and more specifically to partial knee implants and methods for installing the same using instruments.

BACKGROUND

People experiencing knee pain can find relief by way of a partial or full knee replacement surgery, which replaces one or more portions of the person's anatomy with one or more implant components. The present disclosure is directed at solving and/or improving problems with current knee implants and the methods for installation of the such knee implants.

The Unicompartmental-knee arthroplasty (UKA) concept was designed to cause less trauma or damage than traditional total knee replacement by removing less bone and trying to maintain most of the person's bone and anatomy. The concept was also designed to use smaller implants and thereby keep most of the person's bone, with the goal of having them return to normal function faster. A UKA replacement involves replacing only one compartment of the knee. This is a good option in early cases of arthritis where only one compartment (usually the medial) is affected by the arthritic process. The advantage with this type of knee replacement is that it preserves that part of the knee which is not affected by arthritis (e.g., surrounding soft-tissues, cruciate ligaments and contralateral heathy compartment).

Initially, UKAs were not always successful, because the implants were poorly designed, people needing the surgery were not thoroughly screened for suitability, and optimal surgical techniques were not developed. Advancements have been made to improve the design of the implants. Proper patient selection by following the indications/contraindications, and performing the surgery well are key factors for the success of UKA.

UKA is typically suitable for people with moderate joint disease caused by painful osteoarthritis or traumatic injury, a history of unsuccessful surgical procedures, or poor bone density that precludes other types of knee surgery. People who may not be eligible for a UKA include individuals having: an active or suspected infection in or near the knee joint, a known sensitivity to device materials, bone infections or disease that result in an inability to support or fixate the new implant to the bone, inflammatory arthritis, major deformities that can affect the knee mechanical axis, neuromuscular disorders that may compromise motor control and/or stability, any mental neuromuscular disorder, who are obese, lost a severe amount of bone from the shin (tibia) or have severe tibial deformities, recurring subluxation of the knee joint, untreated damage to the knee cap and thigh bone joint (patellofemoral joint), untreated damage to the opposite compartment or the same side of the knee not being replaced by a device, and/or instability of the knee ligaments such that the postoperative stability the UKA would be compromised.

The potential benefits of UKA include a smaller incision because the UKA implants are smaller than the total knee replacements, and the surgeon may make a smaller incision. This may lead to a smaller scar. Another potential benefit is less post-operative pain because less bone is removed. Also, a quicker operation and shorter recovery period may be a result of less bone being removed during the operation and the soft tissue may sustain less trauma. Also, the rehabilitation process may be more progressive. More specific benefits of UKA are that it may improve range of motion, reduce blood loss during surgery, reduce the person's time spent in the hospital, and decrease costs.

Two of the most significant benefits of UKA or partial knee replacements are (1) partial knee replacement subjects report that their replaced knee feels more like their original non-replaced knee as compared to a total knee replacement and (2) partial knee replacements leave other options open to further advances. By not replacing the rest of the knee with metal and plastic, if other options exist in years to come for arthritis in these areas then a partial knee replacement does not burn that bridge.

SUMMARY

According to some implementations, the present disclosure employs a surgical approach that initially requires a tibial cut in flexion of the knee. A proximal tibial resection is performed in extension, using an alignment system. In flexion, the femur gap is measured prior to performing distal resection in extension, which is when the gap balancing process used by the surgeon begins. Spacer blocks and shim build-ups are used to ensure that the minimal tibial implant (e.g., 8 mm) will fit in the flexion space. Once flexion space is balanced and yields the minimal 15 mm gap requirement for the entire system, the distal femur can be resected. In extension, the distal femur is resected using a spacer-block system with modular sliding resection guide blocks (different cut levels in multiple blocks) to address the needed correlation with flexion space. The goal is to resect enough (or as little) of the distal femur as necessary to have a resultant extension gap equal to the measured, resultant flexion gap, which achieves a balanced knee. The next step is to use the multi-purpose femoral preparation guide and trial femoral components to complete the femur resections and peg preparation. The final steps are to size the tibia and complete the tibial preparation with the use of tibial templates that act as a surgical guide for the drilling of the tibial peg holes. The trial femoral components and tibial templates are then removed, and the final tibial baseplate, tibial insert, and femoral condylar implant are installed.

According to one implementation of the present disclosure, a femoral preparation guide is for use on a condyle of a femur during a surgical procedure in which the condyle receives a femoral condylar implant. The femoral preparation guide includes a posterior portion for fitting over a posterior region of the condyle and a distal portion for fitting over a distal region of the condyle. The distal portion is at an angle relative to the posterior portion. The distal portion includes first and second resections slots for receiving cutting tools that provide two resections of the condyle. The first and second resections slots being at angles relative to each other.

According to another implementation of the present disclosure, a femoral preparation guide is for use on a condyle of a femur during a surgical procedure in which the condyle receives a femoral condylar implant. The femoral preparation guide includes a posterior portion for fitting over a posterior region of the condyle and a distal portion for fitting over a distal region of the condyle. The distal portion is at an angle relative to the posterior portion. The distal portion and the posterior portion define a periphery. At least a portion of the periphery substantially matches a portion of an implant periphery of the femoral condylar implant for providing an indication of a position of the femoral condylar implant on the condyle when the femoral condylar implant is subsequently installed on the condyle.

According to a further implementation of the present disclosure, a femoral preparation guide is for use on a condyle of a femur during a surgical procedure in which the condyle receives a femoral condylar implant. The femoral preparation guide includes a posterior portion for fitting over a posterior region of the condyle and a distal portion for fitting over a distal region of the condyle. The distal portion is at an angle relative to the posterior portion. The femoral preparation guide includes a chamfer resection slot on the distal portion for receiving a cutting tool that provides a chamfer surface on the condyle that is angled relative to both the posterior and distal portions. The femoral preparation guide also includes a guide hole for receiving a drill that creates a peg hole that is located on the chamfer surface of the condyle.

In another aspect, the present disclosure is a femoral preparation guide used on a condyle of a femur during a surgical procedure in which the condyle receives a femoral condylar implant. The femoral preparation guide includes a posterior portion for fitting over a posterior region of the condyle. The posterior portion has an attachment element on an underside surface of the posterior portion. A distal portion of the guide fits over a distal region of the condyle. The femoral preparation guide further includes a shim coupled to the attachment element for providing an appropriate joint space to the tibia. The shim is selected from a plurality of shims that are of different sizes.

In a further aspect, the present disclosure is a femoral preparation guide used on a condyle of a femur during a surgical procedure in which the condyle receives a femoral condylar implant. The femoral preparation guide includes a main body for fitting over the condyle. The main body has a slots for guiding resection cuts of the condyle. The main body has a periphery. At least a portion of the periphery substantially matches a portion of an implant periphery of the femoral condylar implant for providing an indication of at least one of (i) a medial-lateral position of the femoral condylar implant that is subsequently installed on the condyle, or (ii) a size of the femoral condylar implant that is subsequently installed on the condyle.

In yet a further aspect, the present disclosure is a set of femoral preparation components for use on a condyle of a femur during a surgical procedure in which the condyle receives a femoral condylar implant. The femoral preparation components include a femoral preparation guide and a femoral trial guide. The femoral preparation guide has (i) a posterior portion for fitting over a posterior region of the condyle, (ii) a distal portion for fitting over a distal region of the condyle, (iii) at least one resection slot for receiving a cutting tool that provides a resection of the condyle, and (iv) a first guide hole for receiving a drill that creates a first peg hole that is located on the condyle. The femoral trial guide is for placement over the condyle after the resection developed with the femoral preparation guide. The femoral trial guide includes a second guide hole for receiving a drill that creates a second peg hole that is located on the condyle. The first and second peg holes for receiving pegs on the femoral condylar implant.

In yet another aspect, the present disclosure is a set of femoral preparation components for use on a condyle of a femur during a surgical procedure in which the condyle receives a femoral condylar implant. The femoral preparation components include a femoral resection guide block, a femoral preparation guide, and a femoral trial guide. The femoral resection guide block slides over a spacer component positioned in region below the condyle. The femoral resection guide block includes a resection slot for receiving a cutting tool that provides a first resection of the condyle. The femoral preparation guide is for attachment to the condyle in the region of the first resection. The femoral preparation guide has two resection slots for receiving cutting tools that provide a second resection and a third resection of the condyle. The femoral preparation guide includes a first guide hole for receiving a drill that creates a first peg hole that is located on the condyle. The femoral trial guide is for placement over the condyle after the resections are developed with the femoral preparation guide. The femoral trial guide includes a second guide hole for receiving a drill that creates a second peg hole that is located on the condyle.

In another aspect, the present disclosure is a femoral trial guide for use on a condyle of a femur during a surgical procedure in which the condyle receives a femoral condylar implant. The femoral trial guide includes a curved outer surface to replicate an outer surface of the femoral condylar implant for providing an indication of the position and movement of femoral condylar implant that is subsequently implanted. The femoral trial guide also includes a guide hole for receiving a drill that creates a peg hole that is located on the condyle.

The present invention also includes the methods of using the femoral preparation components described below and kits of the components described below.

The present invention also includes a kit of components related to the tibial preparation described below.

The present invention further includes a kit of components related to the tibial preparation described below, in combination with the components related to femoral preparation described below.

BRIEF DESCRIPTION OF THE DRAWINGS

The foregoing and other advantages of the present disclosure will become apparent upon reading the following detailed description and upon reference to the drawings.

FIG. 5 illustrates a tibial resection guide attached to the tibia.

FIG. 6 illustrates the tibial resection guide of FIG. 5 in use to make two cuts in the tibia.

FIG. 7 illustrates the resulting two cuts in the tibial plateau from use of the tibial resection guide of FIGS. 5-6.

FIG. 8A illustrates the universal handle that is used for attaching/removing several components in the system and for coupling to measurement tools.

FIG. 8B illustrates the universal handle of FIG. 8A attached to a spacer for measuring the flexion gap between the resected tibia and the femoral condyle.

FIG. 9 illustrates the universal handle attached to a spacer for measuring the extension gap between the resected tibia and the femoral condyle.

FIG. 12 illustrates a gap spacer for measuring the gap between the resected tibia and the resected surface of the femoral condyle.

FIG. 13 illustrates a femoral preparation guide being attached to the resected femoral condyle produced in FIG. 11.

FIG. 14 illustrates the femoral preparation guide of FIG. 13 being used to create a femoral peg hole with a drill.

FIG. 29 illustrates the tibial impactor being used to install the tibial baseplate of FIG. 2.

FIG. 30 illustrates a femoral impactor being used to install the femoral condylar implant of FIG. 4.

FIG. 31 illustrates an insert impactor being used to install the tibial insert of FIG. 3.

FIG. 32A illustrates a first femoral preparation guide of FIG. 13 in relation to the corresponding femoral condylar implant.

FIG. 32B illustrates a second femoral preparation guide of FIG. 13 in relation to a corresponding second femoral condylar implant.

FIG. 32C illustrates a third femoral preparation guide of FIG. 13 in relation to a corresponding third femoral condylar implant.

Figure 1C:
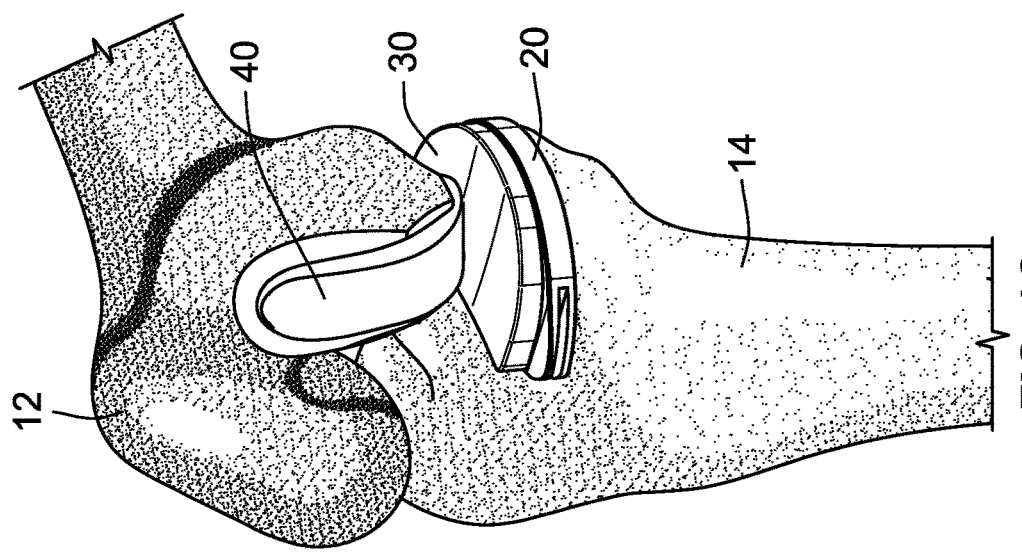
FIG. 1C illustrates the knee of FIG. 1A with the surgical components of FIG. 1B after implantation.

While the present disclosure is susceptible to various modifications and alternative forms, specific implementations have been shown by way of example in the drawings and will be described in further detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Figure 1B:
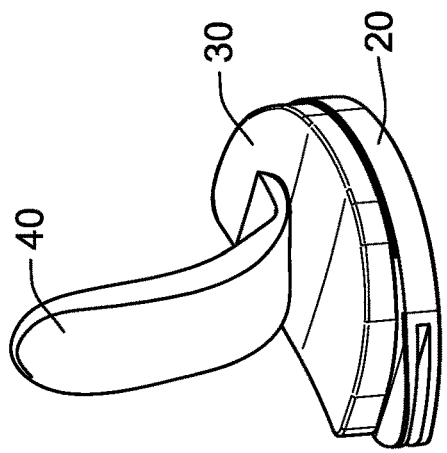
FIG. 1B illustrates the surgical components to be installed on the knee of FIG. 1A in accordance with the present disclosure.
Figure 1A:
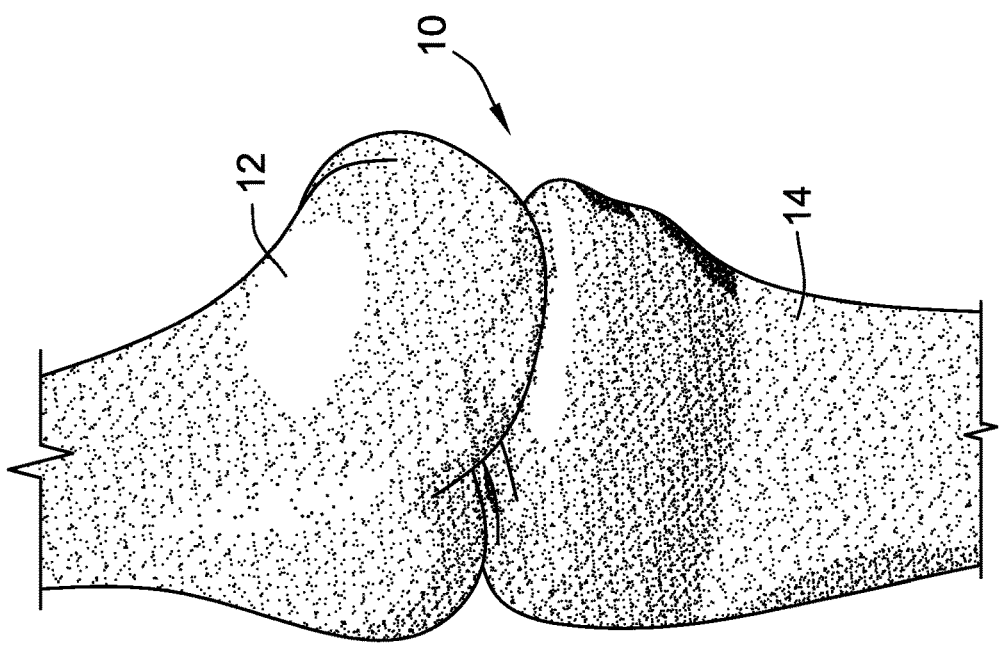
FIG. 1A illustrates a knee that will undergo a UKA procedure in accordance with the present disclosure.

FIG. 1A illustrates a knee 10 that is to undergo a UKA procedure by performing surgical steps on the femur 12 and the tibia 14. FIG. 1B illustrates the final surgical component system to be installed on the knee 10 of FIG. 1A in accordance with the present disclosure. The three components include a tibial baseplate 20, a tibial insert 30, and a femoral condylar implant 40. In FIG. 1C, the tibial baseplate 20, the tibial insert 30, and the femoral condylar implant 40 are illustrated on the tibia 12 and femur 14 after the various procedures outlined in detail below in FIGS. 5-34. The tibial baseplate 20 is mounted on the tibia 14. The tibial insert 30, which is a resilient material, is mated within the tibial baseplate 20. The femoral condylar implant 40 is mounted on the femur 12 and engages the tibial insert 30 by rolling over the tibial insert 30 as the patient flexes the knee.

Figure 2:
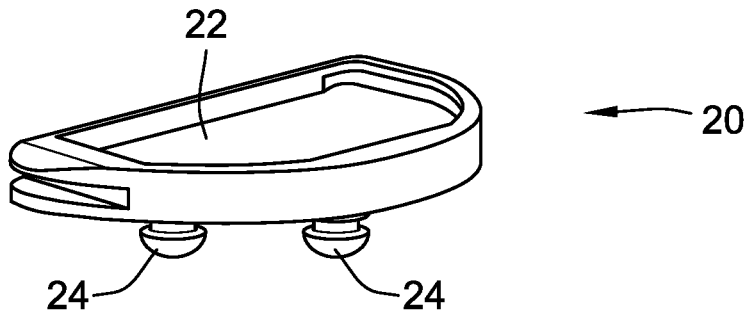
FIG. 2 illustrates the tibial baseplate of the system of FIG. 1B.

FIG. 2 illustrates the details of the tibial baseplate 20 of the system of FIG. 1B. The tibial baseplate 20 has a D-shape and includes a recess 22 on its upper portion. A pair of pegs 24 extend downwardly from its lower portion of the tibial baseplate 20. Although not shown in FIG. 2, a keel (i.e., an extended ridge) extends downwardly from the lower portion of the tibial baseplate 20 along the straight edge of the D-shaped tibial baseplate 20. In one preferred embodiment, the sizing and shaping of the tibial baseplate 20 is optimized according to statistical shape models, and the medial left implant is a mirror image of the lateral right implant.

Figure 3:
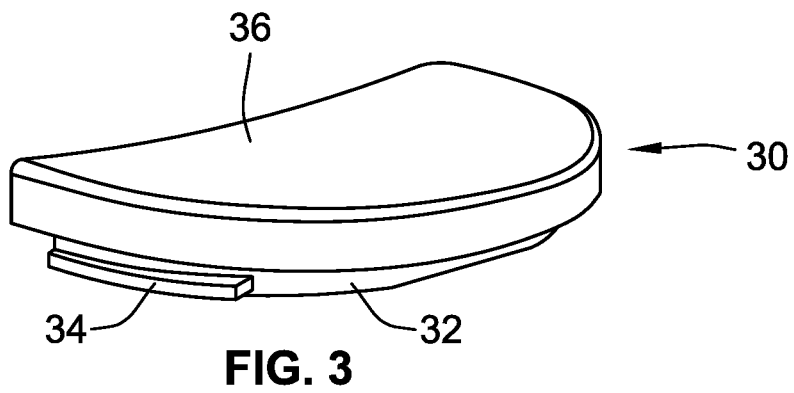
FIG. 3 illustrates the tibial insert of the system of FIG. 1B.

FIG. 3 illustrates the tibial insert 30 that is to be inserted into the recess 22 of the tibial baseplate 20 of FIG. 2. The tibial insert 30 includes a lower projection 32 that tightly fits within the recess 22 of the tibial baseplate 20. Protrusions 34 extend horizontally from the lower projection 32 of the tibial insert 30 and engage corresponding undercuts within the tibial baseplate 20 for assisting with retention on the tibial baseplate 20. The tibial insert 30 is made of a resilient material because it will serve as the engagement surface for the femoral condylar implant 40. The tibial inserts 30 are provided with various thicknesses as part of a kit to help match the anatomy of the patient, as selected by the surgeon. In one preferred embodiment, the tibial insert 30 is labeled for various thicknesses (e.g., 8 mm, 9 mm, 10 mm) and that labeled thickness corresponds to the combined thicknesses of the tibial baseplate 20 and the selected tibial insert 30.

Figure 4:
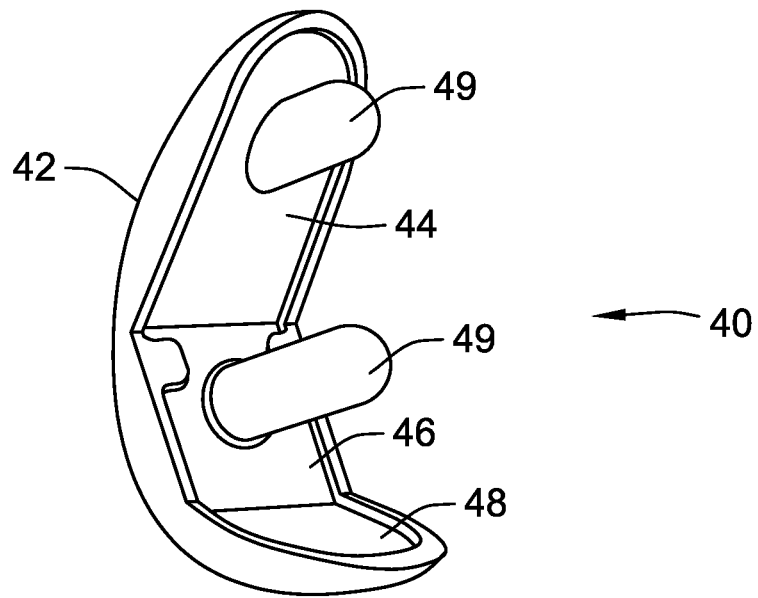
FIG. 4 illustrates the femoral condylar implant of the system of FIG. 1B.

FIG. 4 illustrates the femoral condylar implant 40 that is mounted on the femur 14 in FIG. 1C. The femoral condylar implant 40 includes a rounded exterior surface 42 that mimics the curvature of the bone of the condylar it is replacing. The underside includes a distal surface 44, a middle surface 46, and a proximal surface 48. The underside includes two pegs 49 extending from the distal surface 44 and a middle surface 46. In one preferred embodiment, the sizing and shaping of the femoral condylar implants 40 are optimized according to statistical shape models, and the medial left implant is a mirror image of the lateral right implant.

The bone preparation and trial insertion steps that are undertaken prior to the installation of the tibial baseplate 20, the tibial insert 30, and the femoral condylar implant 40 are generally described relative to FIGS. 5-34.

To prepare the tibia 14, a tibial resection guide 50 is attached to the tibia 14 as shown in FIG. 5. The tibial resection guide 50 is initially retained by use of a distal body ankle clamp (not shown), which is fixed the patient's ankle region and includes an arm that extends toward the knee. This clamp preferably includes adjustment features allowing the tibial resection guide 50 to be adjusted in the medial-lateral (ML) direction and the anterior-posterior (AP) direction so as to achieve propser alignment on the tibia 14. The distal body ankle clamp holds the tibial resection guide 50 in a positon to provide the proper amount bone removal from the tibia 14 as determined by the surgeon.

Once positioned properly aligned, the tibial resection guide 50 is then fixed to the tibia 14 by temporary pins that extend through holes 52 and 54 on the tibial resection guide 50. It also includes a curved portion 56 that extends partially around the tibia 14, providing some lateral stability as well. The upper surface 58 includes a plurality of grooves 59 that provide alignment for the sagittal resection of the tibia. The saw may have features to fit within one of the grooves 59 such that it serves as a guide for a saw 60 that provides the sagittal resection of the tibia 14, as shown in FIG. 6. FIG. 6 also illustrates the upper surface 58 of the tibial resection guide 50 serving as a guide for the saw 62 that provides the transverse resection for the tibia 14.

FIG. 7 illustrates the resulting sagittal resection cut 72 and the transverse resection cut 74 in the tibial plateau from use of the tibial resection guide 50 of FIGS. 5-6. FIG. 7 also illustrates the pin holes 76 that were used to hold the tibial resection guide 50 to the tibia 14.

FIG. 8A illustrates a universal handle 80 that is used to hold various components during the procedure. In FIG. 8B, the universal handle 80 is attached to a spacer device 82 for measuring the flexion gap between the transverse resection cut 74 and the corresponding condyle on the femur 12. In one embodiment, the flexion gap should be at least 8 mm. The flexion gap will approximately correspond to the combined thickness of the tibial baseplate 20 and tibial insert 30 (FIGS. 2 and 3).

In FIG. 9, the universal handle 80 attached to the spacer device 82 for measuring the extension gap between the transverse resection cut 74 and the corresponding section of the condyle on the femur 12. The spacer device 82 can be the same spacer device as in FIG. 8A, or can be a different spacer. The surgeon can use different spacers (e.g., 7 mm, 8 mm, 9 mm, 10 mm) to determine the most accurate measurement for both the flexion gap and the extension gap. The relative measurements of the flexion gap and the extension gap dictates the amount of femur that will be resected.

Figure 10:
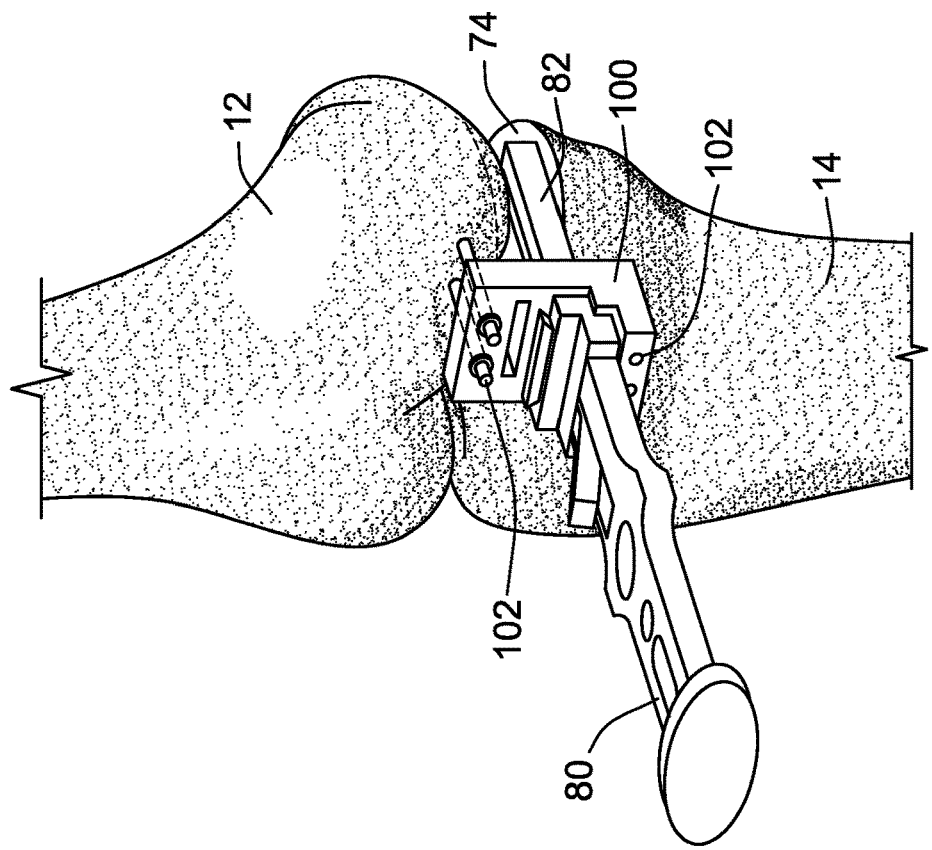
FIG. 10 illustrates the placement of a femoral resection guide block over the spacer in FIGS. 8-9.

FIG. 10 illustrates the placement of a resection guide block 100 that slides over the spacer device 82 in FIG. 9. The resection guide block 100 is selected based on the relative measurements of the flexion gap and the extension gap. For example, if the flexion gap measures 8 mm and the extension gap measures 9 mm, then a −1 mm distal resection guide 100 should be used to achieve a resultant 8 mm extension gap. If the extension gap measures 7 mm, then a +1 mm distal resection guide 100 should be used to achieve a resultant 8 mm extension gap. While the universal handle 80 holds the spacer device 82 and the selected distal resection guide 100 steady, pins 102 are inserted into the femur 12 to hold the distal resection guide 100 to the femur 12 while the knee is in extension.

Figure 11:
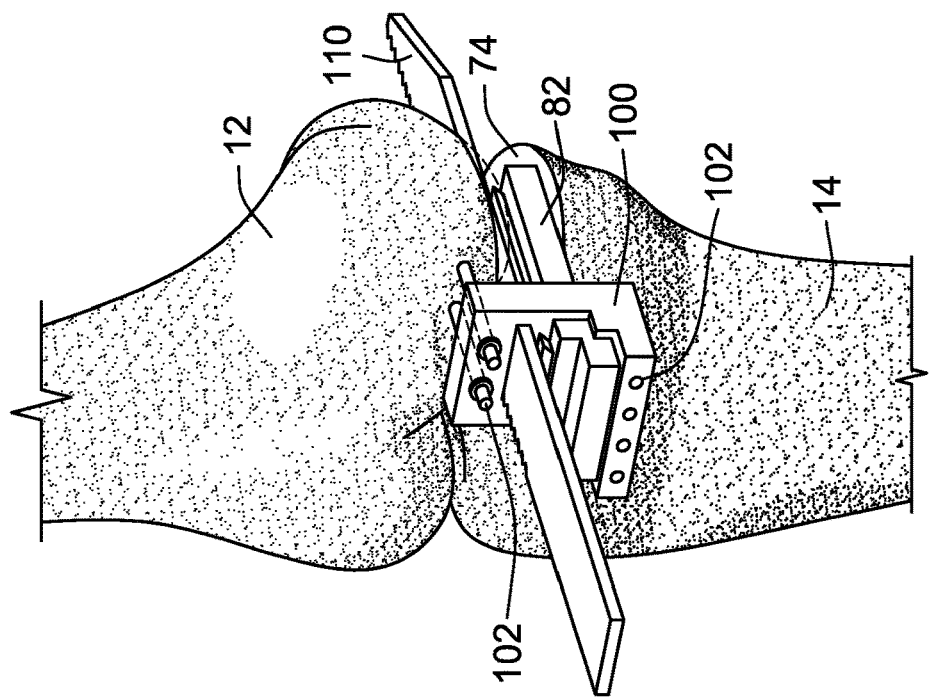
FIG. 11 illustrates the femoral resection guide block of FIG. 10 in use to make a cut in the condyle of the femur.

FIG. 11 illustrates the selected distal resection guide 100 of FIG. 10 after the pins 102 have been attached and the universal handle 80 is removed. A resection saw 110 fits through the distal resection guide 100 to create a transverse cut in the distal portion of the condyle of the femur.

FIG. 12 illustrates a gap spacer block 120 for measuring the gap between the transverse resection cut 74 and a flat distal surface 122 created by the resection saw 110 in FIG. 11. The gap spacer block 120 comes in multiple sizes and correlates to the tibial construct thickness plus the femoral construct thickness. Each gap spacer block 120 provides multiple thicknesses (two per paddle), representing the combined thickness offerings for the femoral condylar implant 40 (e.g., 7 mm) and the tibial insert 30 (e.g., 8, 9, 10 and 12 mm). Therefore, the system would include two gap spacer blocks 120, with a first one having thicknesses of 15 mm and 16 mm, and the second one having thicknesses of 17 mm and 19 mm. As such, if the selected femoral condylar implant 40 (FIG. 4) has a thickness of 7 mm at both the distal and posterior condyles and the selected tibial insert 30 (with the tibial baseplate 20) has a thickness of 8 mm, the gap spacer block 120 having a thickness of 15 mm should fill the gap in FIG. 12.

FIG. 13 illustrates a femoral preparation guide 130 being attached to the resected distal portion of the femoral condyle from FIG. 11. The femoral preparation guide 130 includes a distal portion 131 for fitting over and engaging the flat distal surface 122 of the condyle. The distal portion 131 is pinned to the flat distal surface 122 by a series of through-bores and includes resection slots for received saws, as described below. The posterior portion of the femoral preparation guide 130 includes a lower skid 133 that fits over a posterior region of the condyle. In the illustrated embodiment, the flat inside surface of the distal portion 131 is at an angle of 90° relative to the flat inside surface of the skid 133 of the posterior portion of the femoral preparation guide 130. A peg-hole drill template 132 is located near a junction of the distal portion and the posterior portion. The distal portion of the femoral preparation guide 130 includes a chamfer resection slot 134 and a posterior resection slot 136. Each of these features provide the functionality for the preparation work to be completed on the femoral condyle, as the femoral preparation guide 130 is a multi-purpose component that performs the functions of implant sizing, medial-lateral (ML) positioning, bone resections, and peg-hole preparation.

Regarding the function of implant sizing, the femoral preparation guide 130 enables the surgeon to finalize size selection using the outer profile of the distal portion of the femoral preparation guide 130, which replicates the outer profile of the femoral implants 40 (FIG. 4). The goal is to match and/or correlate the outer profile of the femoral preparation guide 130 with the periphery of the resected distal condyle. The ML position of femoral preparation guide 130 is adjusted until the periphery of distal femur condyle aligns with outer profile of the femoral preparation guide 130. This process is described in more detail with respect to FIGS. 33A-33E.

The size of the femoral preparation guide 130 is selected so there is no under-capping or overhang. Slight under-capping is acceptable, whereas slight overhanging is not preferable and, in most instances, is unacceptable. As such, when femur is between optional sizes for the femoral preparation guide 130, assessing the femur profile with two femoral preparation guides 130 (one is a size smaller and the other is a size bigger) can be accomplished. The smaller femoral preparation guide 130 should then be selected so there is no overhang.

Regarding the functionality of bone resection and peg preparation of the femoral preparation guide 130, after the appropriate size for the femoral preparation guide 130 is selected, it is optimally positioned on the distal resected femoral condyle (from FIG. 11) with its posterior skid sitting flush against the posterior condyle, and its distal surface on the flat distal surface 122 created by the resection with the saw 110 in FIG. 11. The femoral preparation guide 130 is preferably fixed to the bone as follows. Multiple drill bushing holes on the femoral preparation guide 130 accept threaded, headed nails (e.g., 3.2 mm in size). Fixating of the nails into the holes of the femoral preparation guide 130 starts with the most anteriorly located hole; second, to the oblique hole; and third, to the holes located posteriorly (use of one of the two holes depends on whether the left or right condyle is being replaced). In one embodiment, two or three pins are used. Pins located in the anterior and oblique pin holes, by themselves, may be enough for fixation of the femoral preparation guide 130. However, in some instances, the most medial pin hole near the handle attachment is optionally used when surgeon feels additional fixation is required (e.g., in softer bones). Once the femoral preparation guide 130 is attached, the preparation sequence using the femoral preparation guide 130 proceeds with a specific order. This process is also described with reference to FIGS. 33A-33E.

Figure 17:
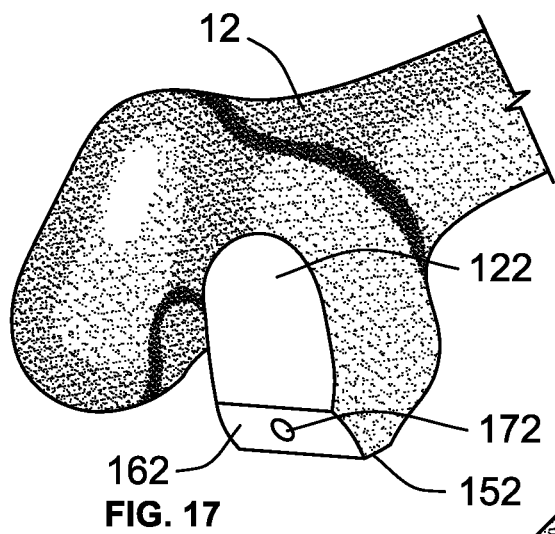
FIG. 17 illustrates the resulting three flat surfaces on the femoral condyle from cuts in FIGS. 11, 15, and 16.

Referring to FIG. 14, the femoral preparation guide 130 is used to create a femoral peg hole with a drill guide 140 that attaches around the peg-hole drill template 132. From the posterior end of the femoral preparation guide 130, a peg hole is drilled with a drill 142 that fits within the drill guide 140. The guide 140 has an upper boss that provides the desired peg hole depth when the stop element on the drill 142 engages the boss. The peg hole will be on the chamfer surface 162, as shown in FIG. 17.

Figure 15:
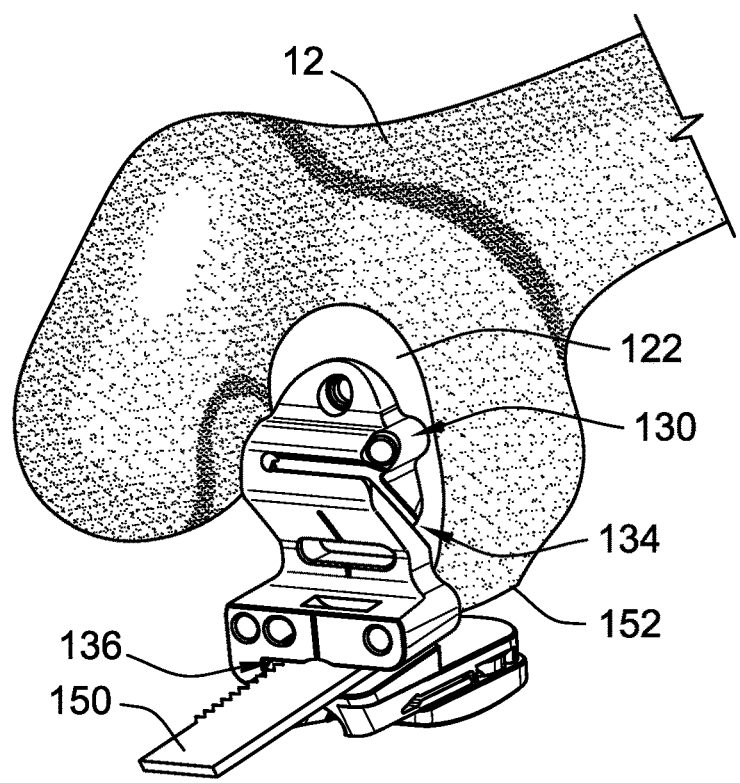
FIG. 15 illustrates the femoral preparation guide of FIG. 13 being used to create a posterior resection.
Figure 16:
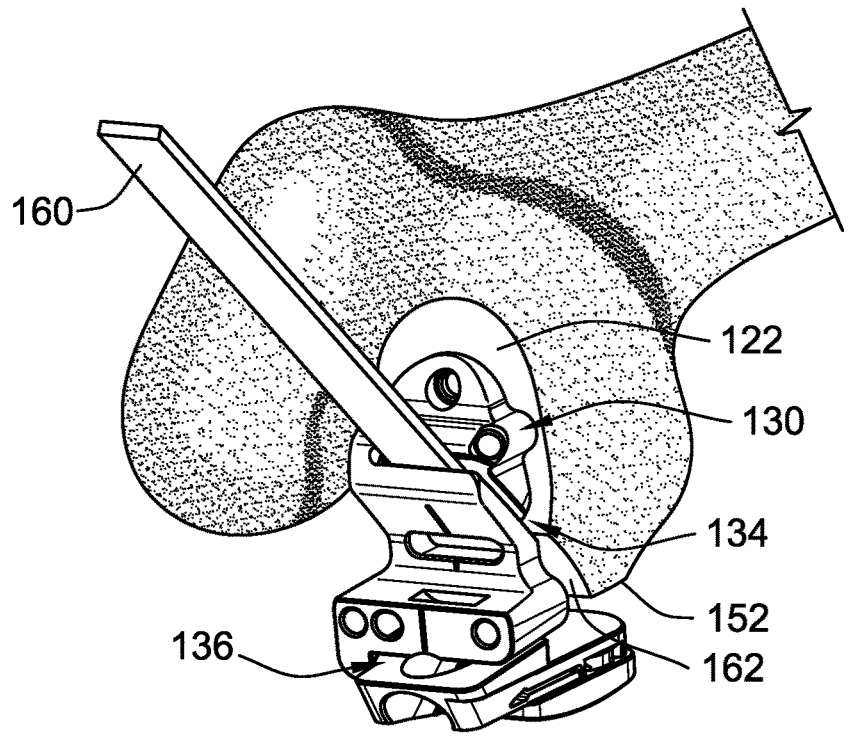
FIG. 16 illustrates the femoral preparation guide of FIG. 13 being used to create a posterior chamfer resection.

Referring to FIG. 15, the femoral preparation guide 130 if used to create a posterior resection of the posterior condyle with a saw 150. A flat posterior surface 152 is created by the saw 150, extending across the condyle and providing a clearance opening for the posterior chamfer resection process (FIG. 16). As shown best in FIG. 33E (described below), the posterior portion (i.e., the lower skid) of the femoral preparation guide 130 is at 90 degrees to the distal vertical plane of the guide 130. The posterior resection slot 136 is angled at about 5 degrees from this posterior lower skid of the femoral preparation guide 130. Thus, the flat posterior surface 152 is at approximately at an 85° angle with respect to the flat distal surface 122. This clearance functionality is important because it ensures the chamfer saw does not continue cutting though the condyle and into the posterior metal skid of the femoral preparation guide 130. This feature and functionality are illustrated in more detail in FIGS. 33A-33E.

In FIG. 16, the femoral preparation guide 130 is then used with a saw 160 to create a posterior chamfer surface 162. The chamfer surface 162 extends between the flat distal surface 122 and the flat posterior surface 152, as shown best in FIG. 17. In the illustrated embodiment, the chamfer surface 162 is at an angle of approximately 45 degrees with respect to the flat distal surface 122. FIG. 17 also shows the chamfer peg hole 172 that is later used to receive one of the pegs of the femoral implant 40 (FIG. 4). Additionally, the chamfer peg hole 172 is used to receive the femoral trial guide 180 of FIG. 18. The reason for this is to allow the surgeon to perform positional adjustment using the femoral trial guide 180 prior to completing the preparation.

Figure 18:
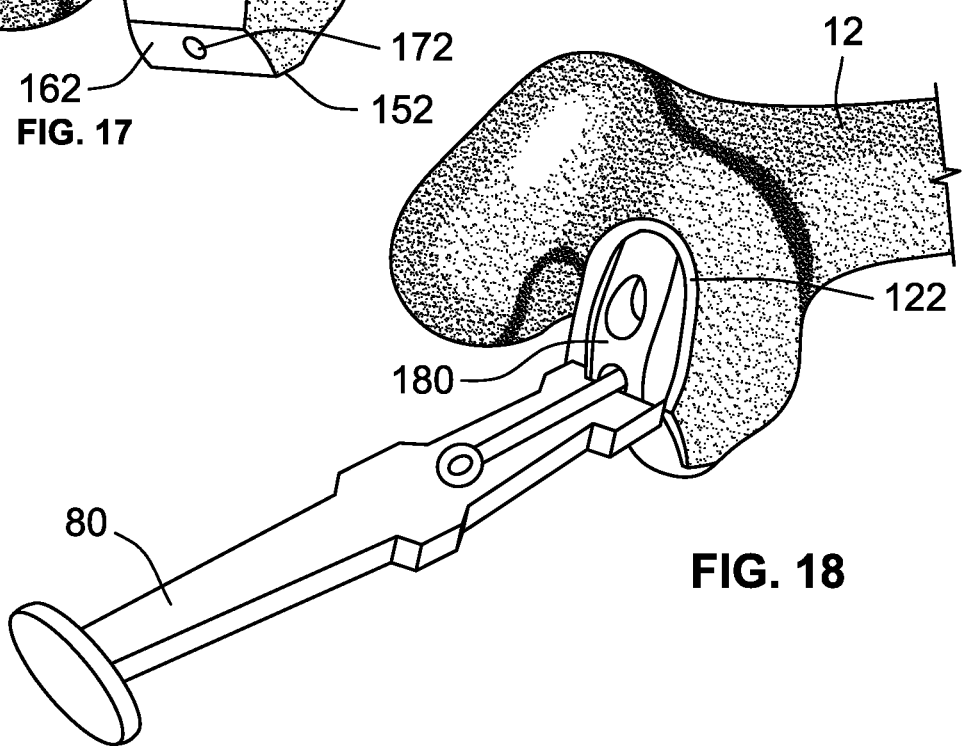
FIG. 18 illustrates the universal handle being used to attach a femoral trial guide.
Figure 19:
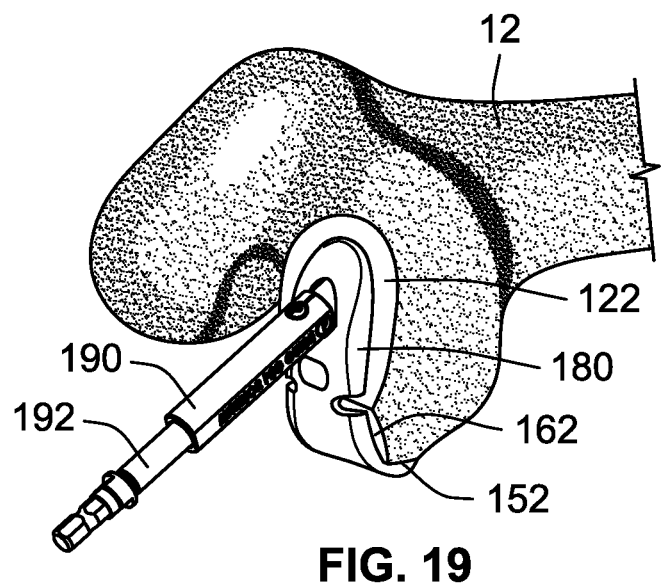
FIG. 19 illustrates the femoral trial guide being used to create hole in the femoral condyle.

FIG. 18 illustrates the universal handle 80 being used to attach the femoral trial guide 180. The final femoral preparation is completed using the femoral trial guide 180 as it assists in the development of the distal peg hole preparation, as shown in FIG. 19. On the underside of the femoral trial guide 180, there are three flat surfaces to engage the flat distal surface 122, the flat posterior surface 152, and the chamfer surface 162. The underside of the femoral trial guide 180 also includes a peg to mate with the chamfer peg hole 172 (FIG. 17).

In FIG. 19, the femoral trial guide 180 provides the functionality of creating the distal peg preparation when used with a drill guide 190. After the drill guide 190 is attached to the femoral trial guide 180, a drill 192 is used to create a distal peg hole in the femoral condyle. The femoral trial guide 180 and the drill guide 190 provide for alignment and depth control during peg-hole preparation with the drill 192.

Figure 20:
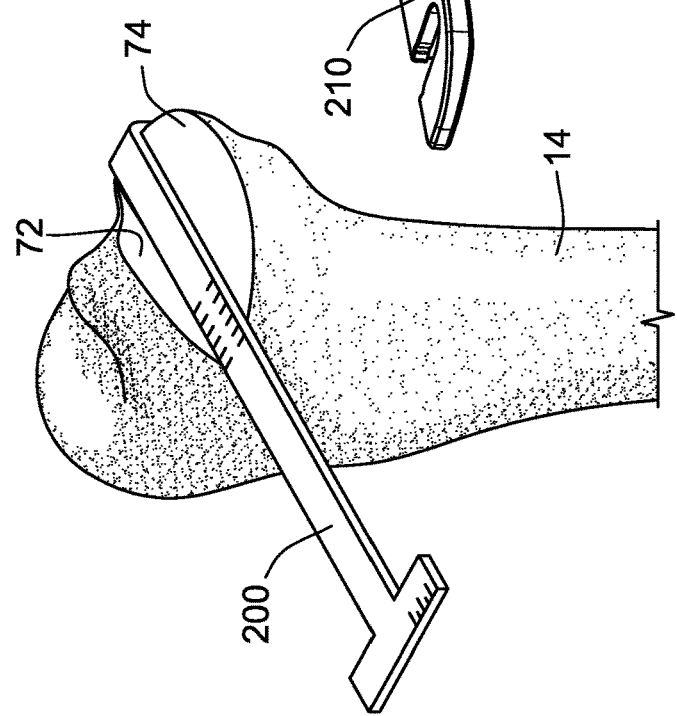
FIG. 20 illustrates the resected tibial plateau being measured for the correct size for the final tibial baseplate and tibial surgical template.

FIG. 20 illustrates the use of a tibial sizer 200 that measures the dimensions of the transverse surface 74 in the posterior-anterior direction and the medial-lateral direction. The measurements ensure the selection of the correct size for the tibial surgical template 220 (FIG. 20) and the tibial baseplate 20 (FIG. 2). If necessary, an additional sagittal cut of the tibia that is distal to the existing sagittal surface 74 may be needed to ensure proper space.

Figure 21:
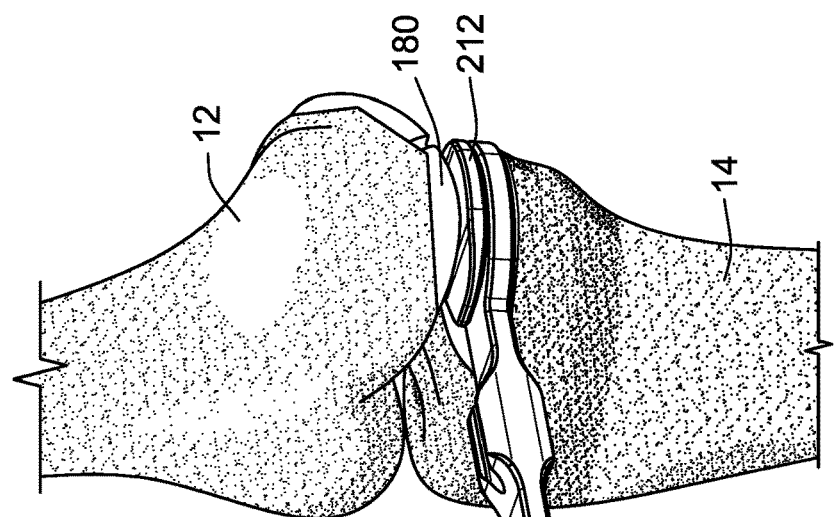
FIG. 21 illustrates a tibial spacer base and shims for measuring the gap and soft-tissue tension in flexion and extension

FIG. 21 illustrates a tibial spacer base 210 having shims 212 that is used the measure the space from the transverse surface 74 on the tibia 14 to the trial femoral guide 180. Different sizes of shims 212 may be locked into the tibial spacer base 210 through a rotating motion that locks mating features (e.g., like a bayonet-key connection) or through a dovetail connection. These measurements with the spacer base 210 and the shims 212 ensure the proper selection of sizes for the tibial surgical template 220 (FIG. 20), the tibial baseplate 20 (FIG. 2), and the tibial insert 30 (FIG. 3).

Figure 22:
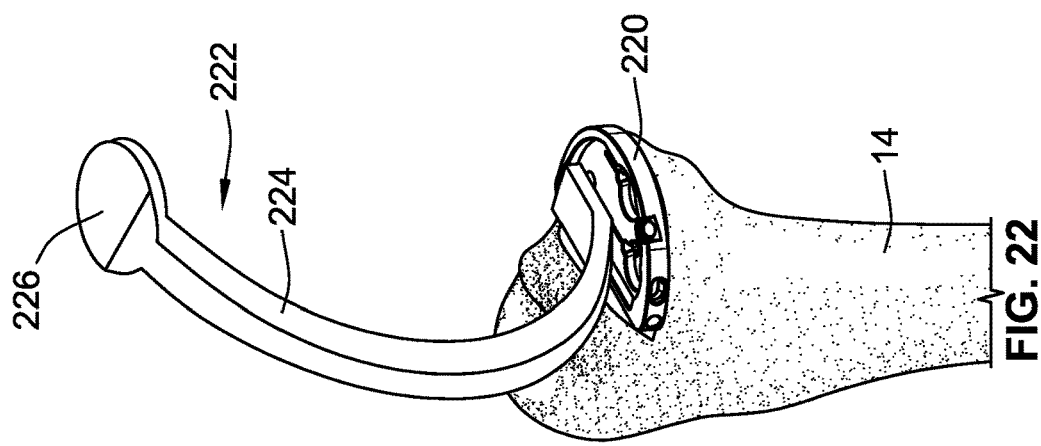
FIG. 22 illustrates a tibial impactor being used to install on a tibial surgical template on the resected tibial plateau.

FIG. 22 illustrates the tibial surgical template 220 on the resected tibial plateau being installed with a tibial impactor 222. The tibial surgical template 220 includes features allowing it to temporarily mate with the tibial impactor 222 during installation. The tibial impactor 222 includes a flexible arm 224 and a handle 226. When force is placed on the handle 226, the force is transmitted along the arm 224 and forces protrusions, such as a keel (not shown), on the bottom of the tibial surgical template 220 into the bone. As will be discussed below, the tibial surgical template 220 acts as a guide for prepping the tibia, and also serves as a trial tibial baseplate prior to the final installation of the tibial baseplate 20.

Figure 23:
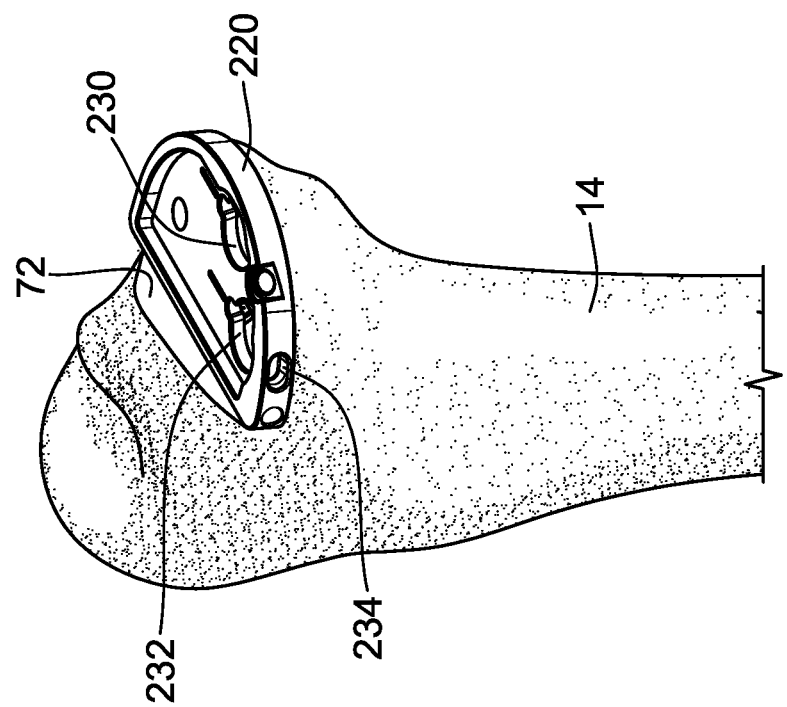
FIG. 23 illustrates the tibial surgical template on the resected tibial plateau after the process of FIG. 22.
Figure 26:
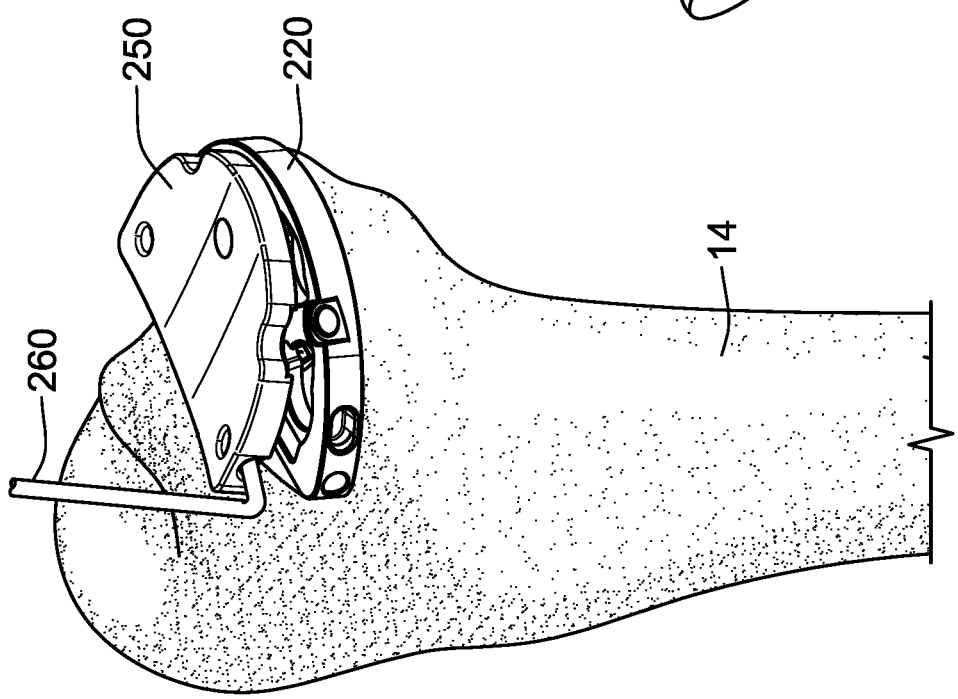
FIG. 26 illustrates the tibial trial insert being removed from the tibial surgical template.

FIG. 23 illustrates the tibial surgical template 220 on the resected tibial plateau after placement by the tibial impactor 222 of FIG. 22. The tibial surgical template 220 includes openings 230, 232 that allow for the development of peg holes to be used with the pegs 24 on the final tibial baseplate 20 (FIG. 2). It also includes side openings 234 that allow for better removal of trial inserts, as shown in FIG. 26. The side openings 234 also provide for pin fixation, which stabilizes the surgical template 220 on the proximal bone surface prior to peg preparation and trialing.

Figure 24:
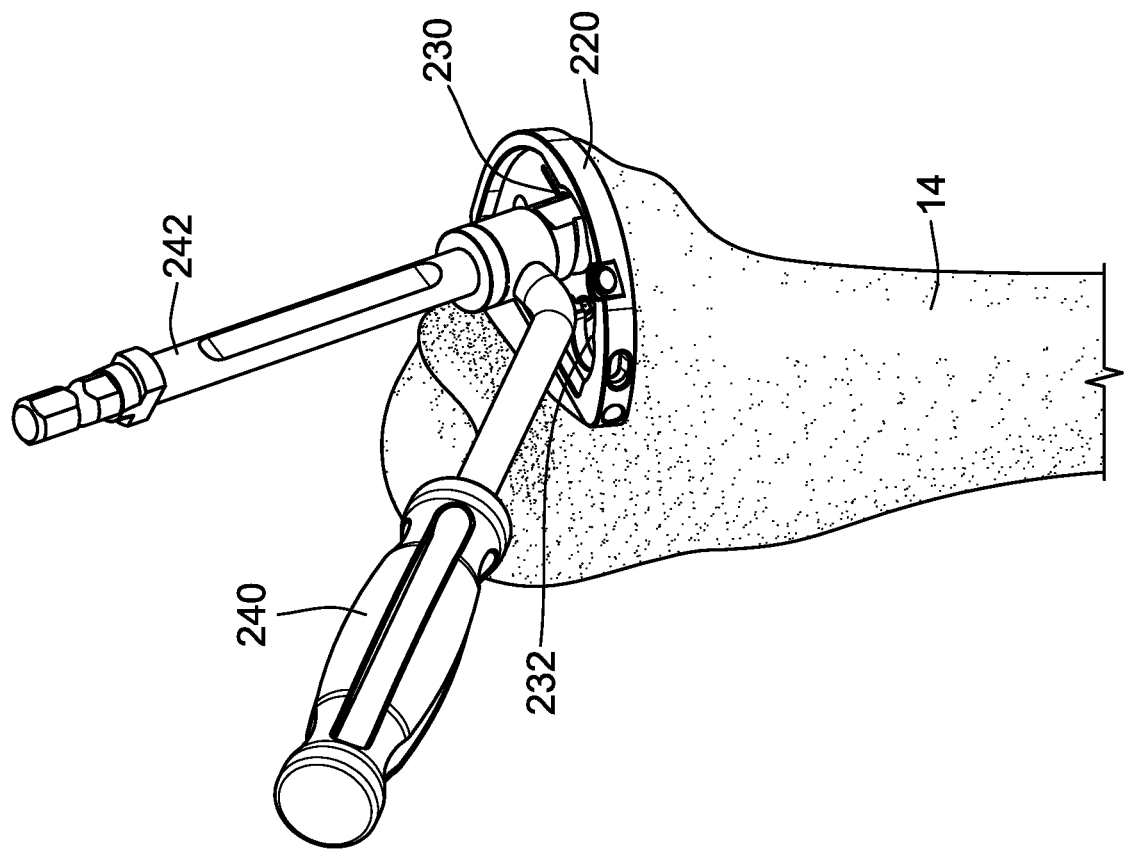
FIG. 24 illustrates the tibial surgical template and a drill guide being used to create a hole in the resected tibial plateau.

FIG. 24 illustrates a drill guide 240 that has been mated with the opening 230 in the tibial surgical template 220. A drill 242 is placed through the drill guide 240 used to create a hole in the resected tibial plateau that will receive one of the pegs 24 (FIG. 2) on the final tibial baseplate 20. A second peg hole in the bone is created by use of the drill 242 and the drill guide 240 on the opening 232.

Figure 25:
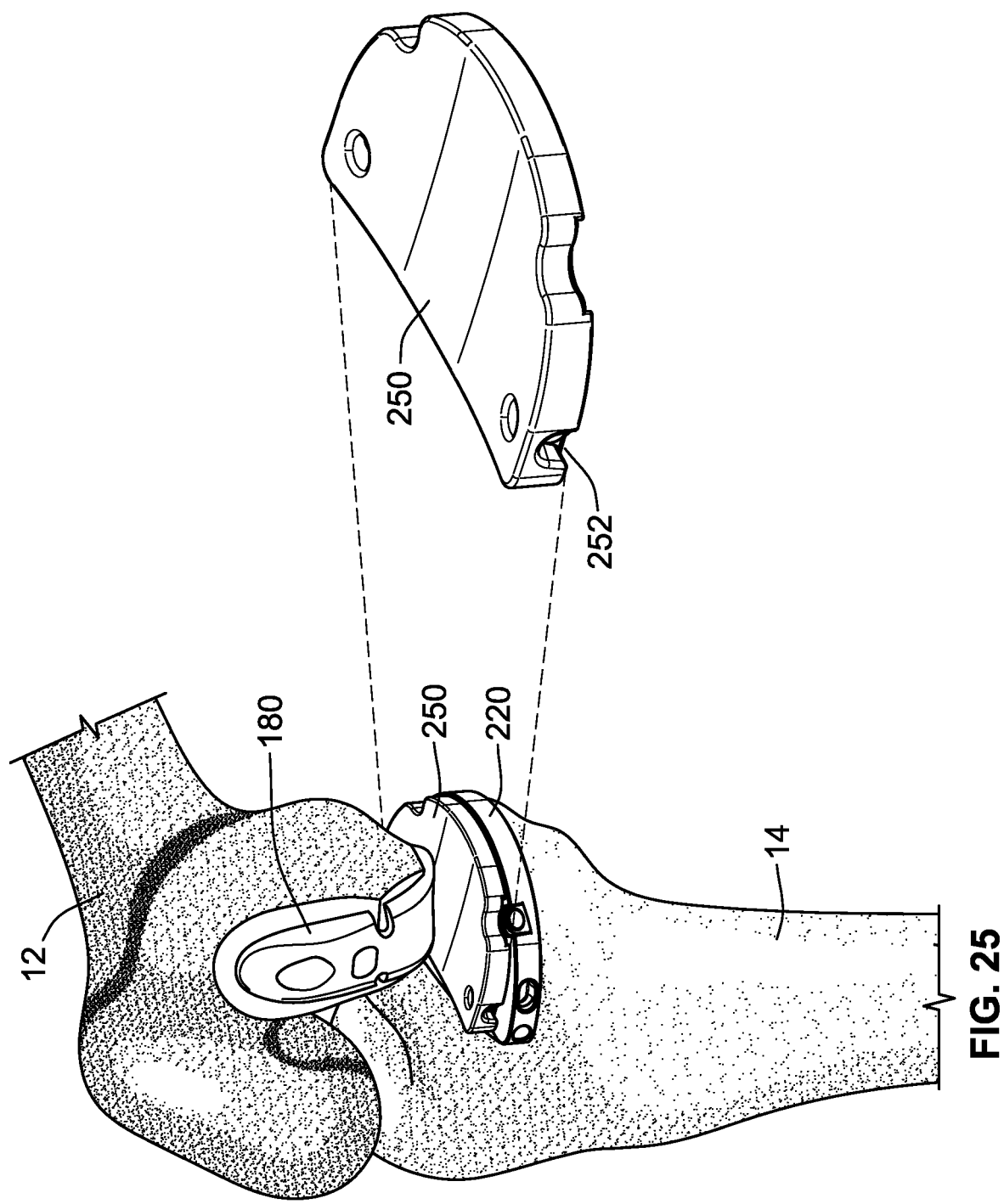
FIG. 25 illustrates the tibial surgical template and a tibial trial insert for testing the relationship to femoral trial guide prior to the installation of final implant components.

FIG. 25 illustrates the tibial surgical template 220 in use with a tibial trial insert 250. Because the femoral trial guide 180 substantially replicates the femoral implant 40 (FIG. 4), and the tibial surgical template 220 and the trial tibial insert 250 substantially replicate the tibial baseplate 20 (FIG. 2) and tibial insert 30 (FIG. 3), respectively, the components illustrated in FIG. 25 provide the surgeon with a better understanding of how the final implants will work prior to their final installation. Thus, any bone or component adjustments can be made before the final installation. In effect, the tibial surgical template 220 and the femoral drill guide 180 are both surgical templates for drilling holes and trial implants. The tibial insert 250 includes various openings and cutouts 252 to allow it to be removed from the tibial surgical template 220 and to provide for clearance for pins that secure the tibial surgical template 220 to the bone.

Figure 27:
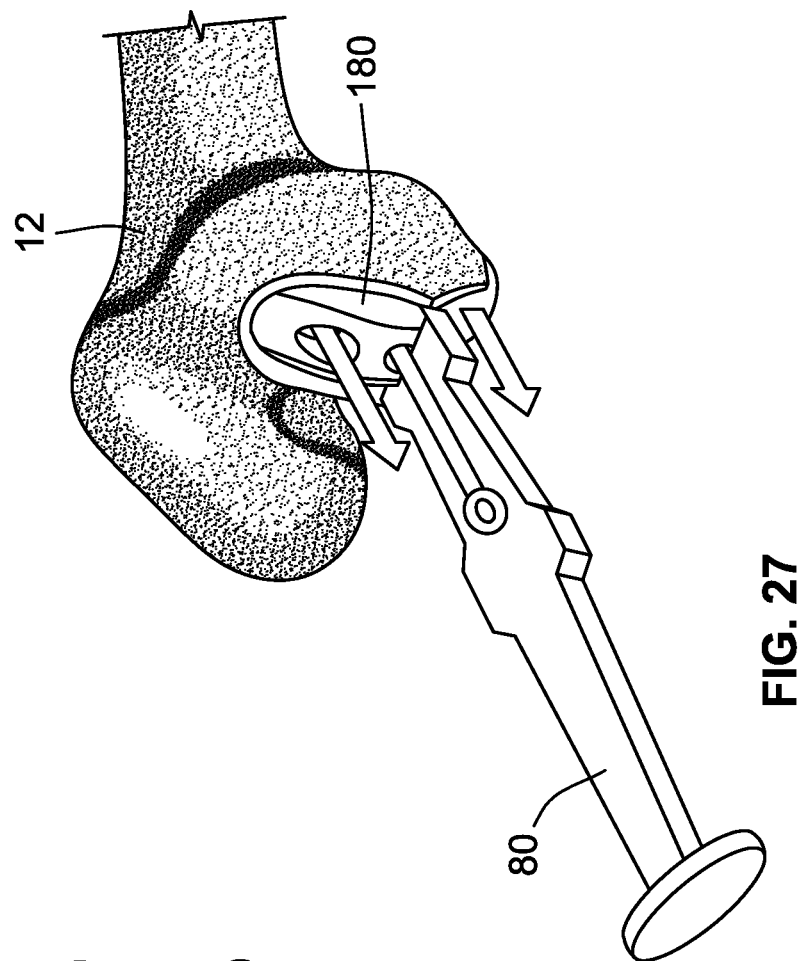
FIG. 27 illustrates the universal handle being used to remove the femoral trial guide.

FIG. 26 illustrates the tibial trial insert 250 being removed from the tibial surgical template 220 by use of a tool 260. After the tibial trial insert 250 is removed, the tibial surgical template 220 can be removed from the tibia by use of common surgical tools, such as kochers. FIG. 27 illustrates the universal handle 80 as it is used to remove the femoral trial guide 180 from the femur 12.

Figure 28:
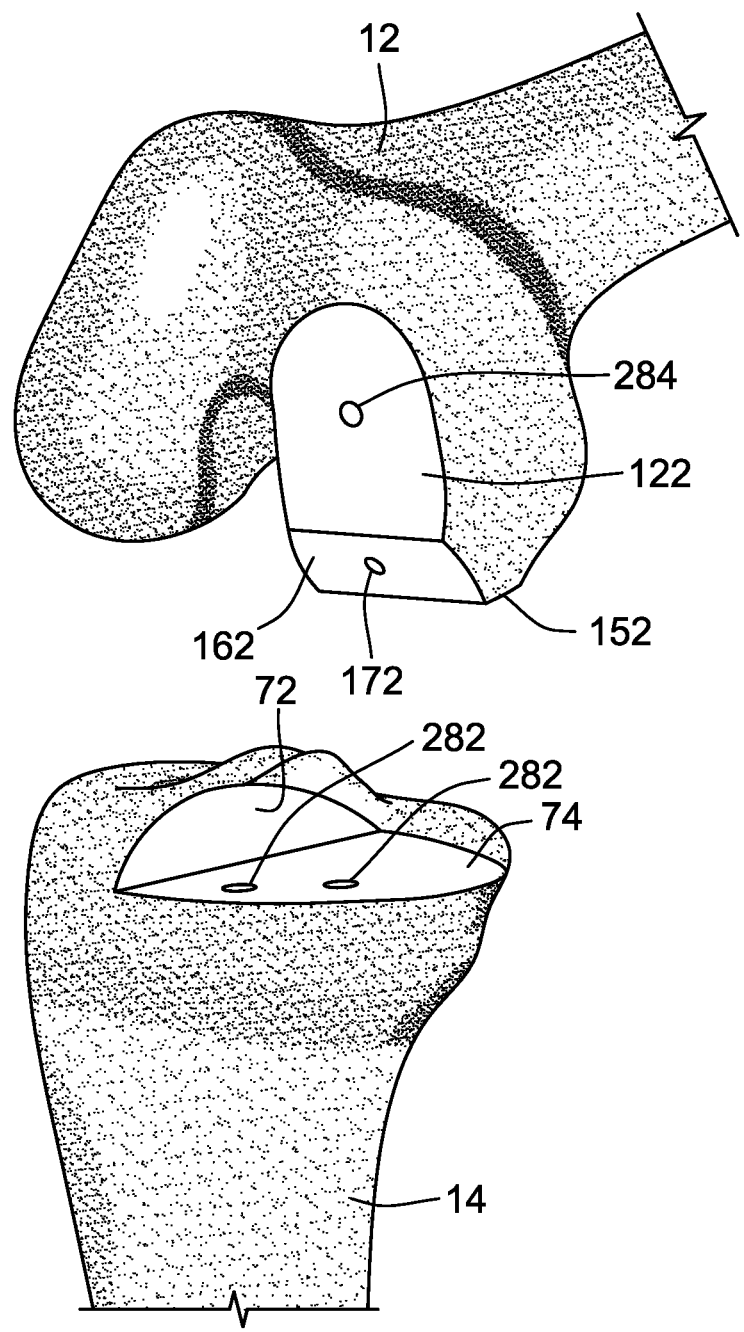
FIG. 28 illustrates the resulting three surfaces in the femoral condyle along with the femoral peg holes, and the resulting two surfaces in the tibial plateau along with the tibial peg holes.

FIG. 28 illustrates the preparation of the femur 12 and the tibia 14 after the femoral trial guide 180 and tibial surgical template 220 have been removed. The femoral condyle includes three flat surfaces (the flat distal surface 122, the flat posterior surface 152, the chamfer surface 162) and two peg holes 172 and 284. The first chamfer peg hole 172 was produced with the drill 142 and the femoral preparation guide 130, as shown in FIG. 14. The second peg hole 284 was produced by the femoral trial guide 180 with the drill 190 in FIG. 19. The tibia 14 includes the transverse surface 74 and the sagittal surface 72, and the two peg holes 282 created by the drill 242 and the tibial surgical template 220 in FIG. 24.

FIGS. 29-31 illustrate the placement of the final implant components. FIG. 29 illustrates the tibial impactor 222 being used to install the tibial baseplate 20. In one preferred embodiment, bone cement is applied thoroughly to the prepared bone surfaces of the tibia 12, including the peg holes 282 (FIG. 28). Cement is also applied to the underside of the tibial baseplate 20, including the pegs 24 (FIG. 2) that fit into the peg holes 282 and other protrusions (e.g., keels). Cement should cover these surfaces sufficiently to optimize implant fixation to the bone FIG. 30 illustrates a femoral impactor 302 that is used to install the femoral condylar implant 40 of FIG. 4. Cement should be applied thoroughly to both the prepared bone surfaces of the femur (the flat distal surface 122, the flat posterior surface 152, the chamfer surface 162) and the two peg holes 172 and 284. Cement is also applied to the underside of the femoral condylar implant 40, including the pegs 48 (FIG. 4) that fit within the two peg holes 172 and 284. The femoral impactor 302 is used to force the femoral condylar implant 40 into its final position.

FIG. 31 illustrates an insert impactor 312 that is used to install the tibial insert 30 into the tibial baseplate 20. As shown in FIG. 3, the tibial insert 30 includes structures 34 (See FIG. 3) that allow it to mate with corresponding features in the tibial baseplate 20 so that the tibial insert 30 is properly retained. At this point, the partial-knee implant has been installed in the patient.

FIGS. 32A-32C illustrate three femoral preparation guides 130a, 130b, 130c in relation to their corresponding femoral condylar implants 40a, 40b, 40c. As noted above, the femoral preparation guides 130 replicate the contours of the femoral condylar implants 40 to provide the proper the implant sizing and ML positioning before the appropriate femoral condylar implant 40 is installed. In one preferred embodiment, each femoral preparation guide 130 has a corresponding singular femoral condylar implants 40. Thus, as shown in FIGS. 32A-32C, the three femoral preparation guides 130a, 130b, and 130c correspond, respectively, to only three condylar implants 40a, 40b, 40c. The present invention contemplates having more than three matching pairs of femoral preparation guides 130 and condylar implants 40.

In another preferred embodiment, each femoral guide 130 has a shape and size that represents the peripheries of two different femoral condylar implants 40, such that three femoral preparation guides 130a, 130b, 130c are useful with six condylar implants 40. For example, the three femoral guide 130a, 130b, 130c are sizes 1, 3 and 5, but cover sizes 1, 2, 3, 4, 5, 6 for the condylar implants 40. In other words, each femoral guide 130 is the same size as one condylar implant 40, and is close in size to the next larger size of condylar implant 40. The small femoral guide 130a matches the periphery of size 1 of the condylar implant 40, but covers sizes 1 and 2 of the condylar implants 40. The medium femoral guide 130b matches the periphery of size 3 of the condylar implant 40, but covers sizes 3 and 4 of the condylar implants 40. The large femoral guide 130c matches the periphery of size 5 of the condylar implant 40, but covers sizes 5 and 6 of the condylar implants 40. As a result, a surgeon is able to quickly assess between two size groups. For example, the small guide 130a is same as implant size 1. So if the small guide 130a is too small, then the patient's knee likely requires size 2 of the condylar implants 40. By then placing the medium guide 130b (size 3) near the installation site, the surgeon will then know whether size 3 is too large, leading the surgeon to definitely know that size 2 for the condylar implant 40 is needed. As such, the surgeon will use the small preparation guide 130*a* (size 1), and a femoral drill guide 180 and a condylar implant 40 that is size 2.

Figure 33B:
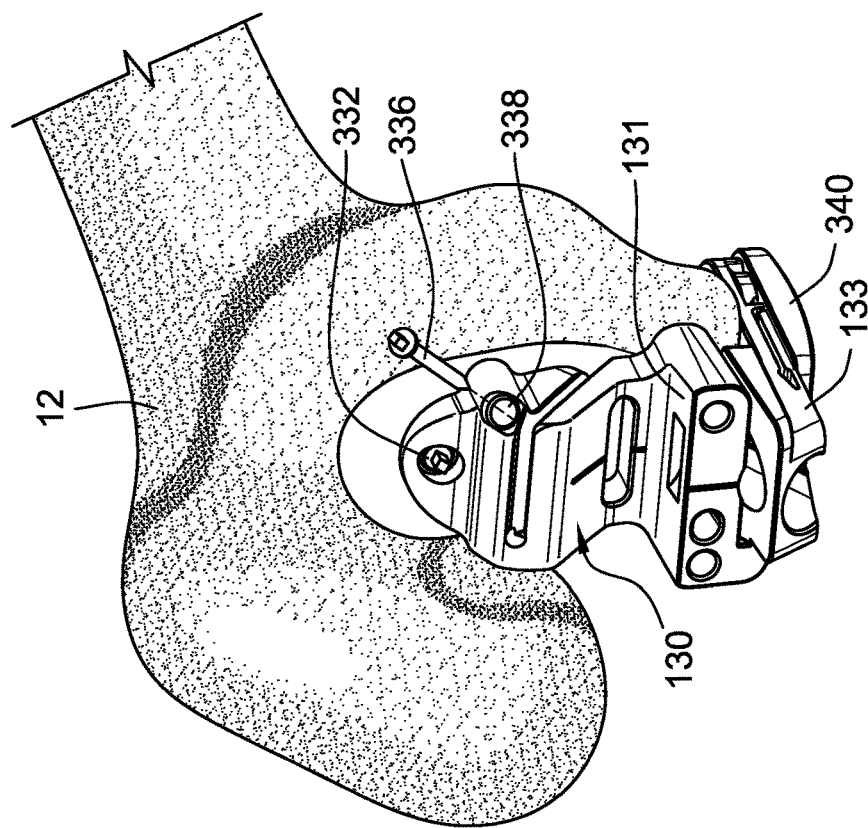
FIG. 33B illustrates additional details of the attachment of the femoral preparation guide of FIG. 13 to the femoral condyle.
Figure 33A:
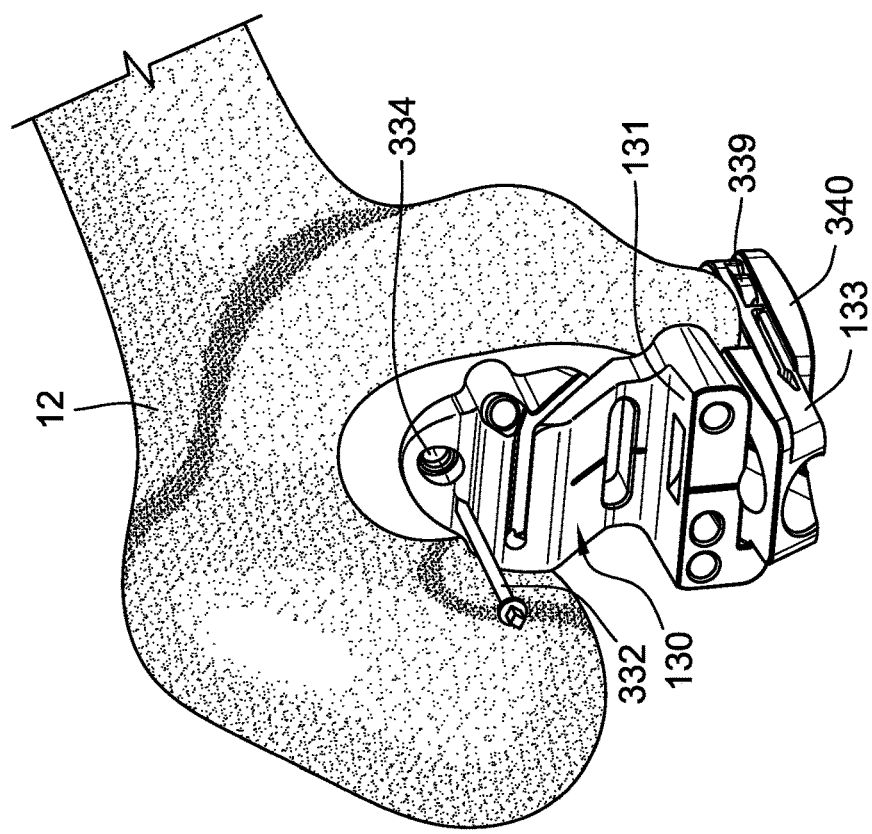
FIG. 33A illustrates details of the attachment of the femoral preparation guide of FIG. 13 to the femoral condyle.

FIGS. 33A-33E illustrate more details of the attachment of the femoral preparation guide 130 to the femur 12 and its use on the femoral condyle. FIGS. 33A and 33B illustrate the initial placement of the first pin 332 into the most anterior-located through-bore 334 of the distal portion 131 of the femoral preparation guide 130, and the placement of the second pin 336 into the oblique through-bore 338 of the distal portion 131. The second pin 336 is guided into the oblique through-bore 338 at a different angle than the first pin 332 to help retain the femoral preparation guide 130 in multiple directions. FIGS. 33A-33B also illustrate one size of shim 340 that include features to mate within the recess or slot 339 in the posterior skid 133 of the femoral preparation guide 130. These are described in detail in FIGS. 34A-34B. When the shim 340 is wedged into the joint space, the use of only the first pin 332 and the second oblique pin 336 is needed to secure the femoral preparation guide 130. When bone is soft (i.e., osteopenic), the surgeon may choose to use a third fixation pin in one of the three lower holes in the distal portion 131. Generally, the use of a third pin in the most medial hole of the three lower holes will suffice for attachment.

The bone preparation and guide stability functions of the femoral preparation guide 130 at least partially rely on the order of stabilizing and fixating guide 130 in and anterior to posterior sequence and then using the opposite order (posterior to anterior) for the actual preparation of the bone. The specific sequence of steps for fixing the guide (anterior to posterior) and the subsequent bone-preparation steps (posterior to anterior) ensures the femoral preparation guide 130 remains stable. By placing the anterior-most first pin 332, it provides the necessary initial stability needed prior to placing the oblique pin (guide screw) 336. Without the anterior-most first pin 332, the femoral preparation guide 130 has a tendency to shift when placing the oblique pin/guide screw 336. After pinning the anterior-most through-bore 334 and the oblique through bore 338, a third pin can be used in the most medial hole of the three lower holes in some instances when the bone is soft. In addition to the sequence of steps, the use of sagittal curved shims 340 facilitates the stability of the steps for preparing the bone. The specific sequence also allows for final refinement of the implant position, which includes the final peg hole that is drilled through femoral trial guide. Regarding preparation of the surfaces and peg holes, the peg-hole drilling is preferably completed first to ensure accuracy, because once bone resections are made, the precise fixation of the femoral preparation guide 130 on the bone may be sacrificed. The posterior resection is completed before the posterior chamfer resection because, with the posterior condyle bone removed, the surgeon will be able sense when the chamfer resection is completed well before saw blade contacts runs into metal posterior skid of the femoral preparation guide 130, as shown in FIG. 33E. Thus, the posterior resection that creates the posterior flat surface 152 provides for the clearance for the chamfer saw 160.

Figure 33C:
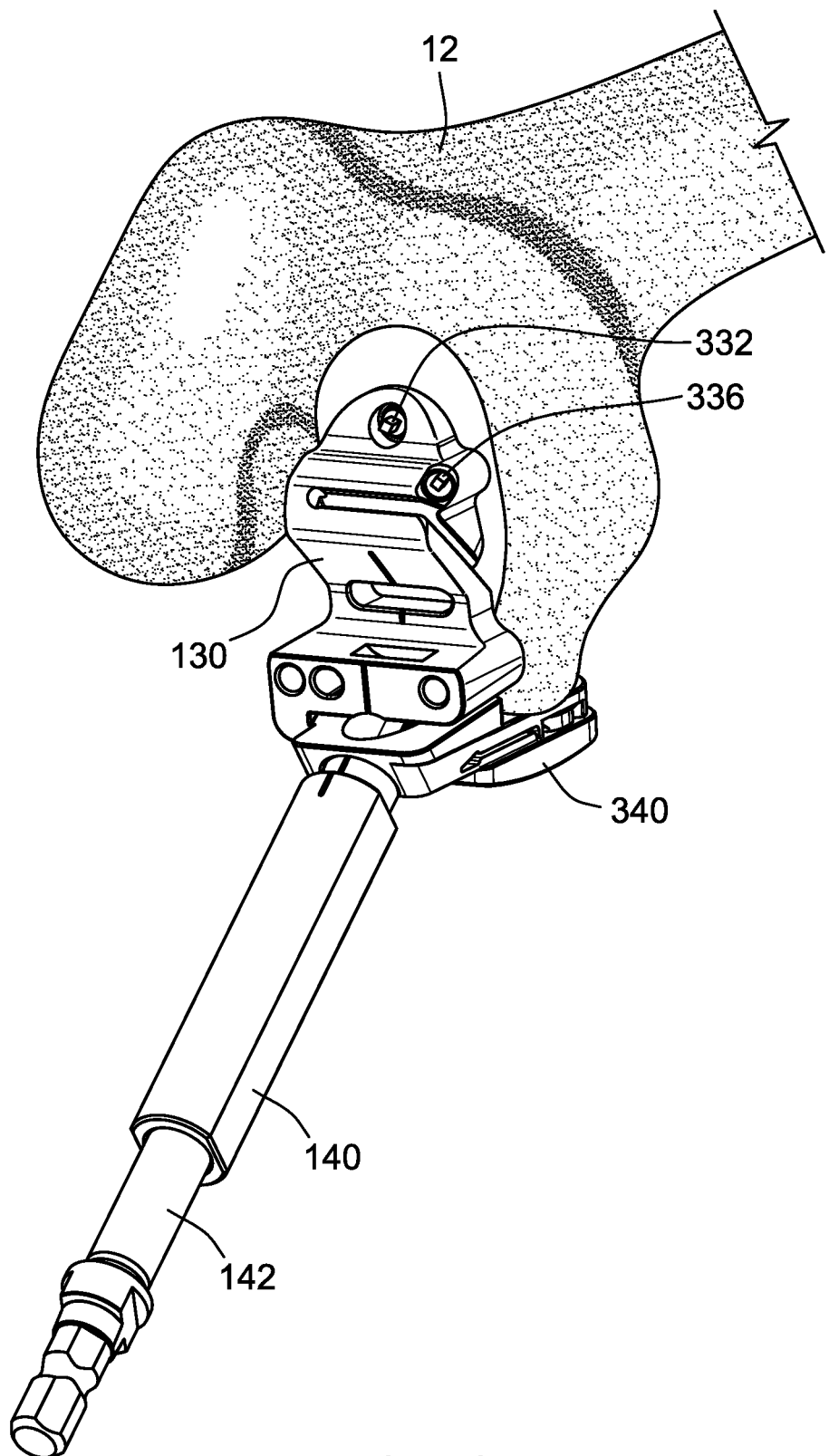
FIG. 33C illustrates the use of the femoral preparation guide of FIG. 13 to help guide the drilling of the peg hole.
Figure 33E:
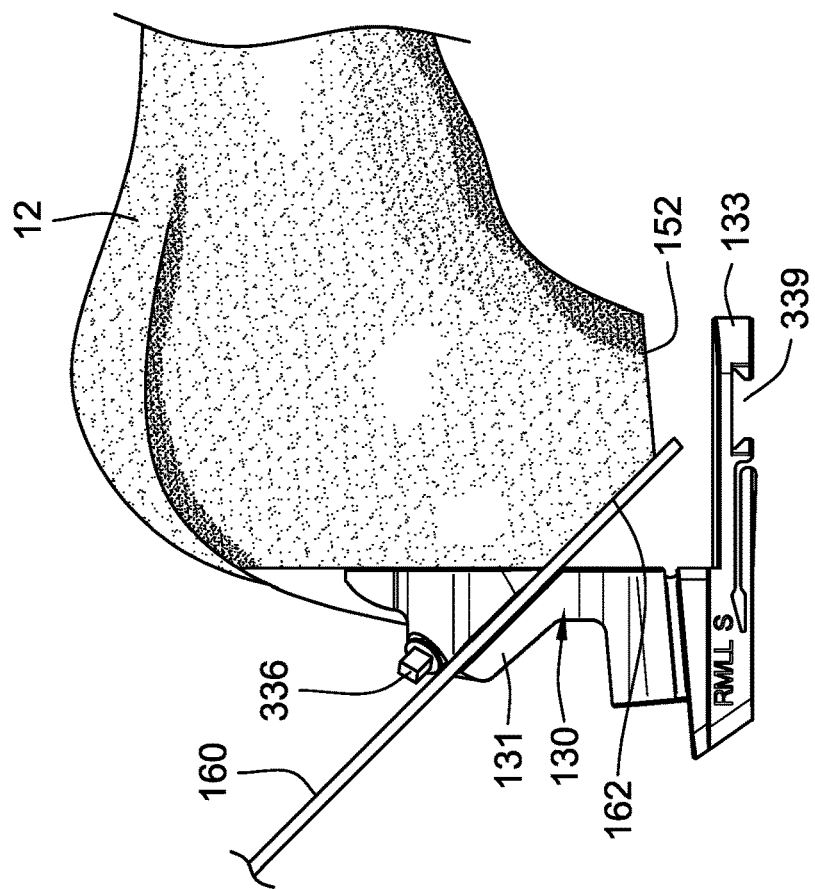
FIG. 33E illustrates the use of the femoral preparation guide of FIG. 13 in creating the posterior chamfer resection in more detail.

FIG. 33C illustrates the use of the femoral preparation guide 130 while drilling a peg hole with the use of the drill guide 140 and the drill 142. The first pin 332 and the second pin 336 are placed at locations and angles that do not interfere with the drill 142 as it advances into the femur 12.

Figure 33D:
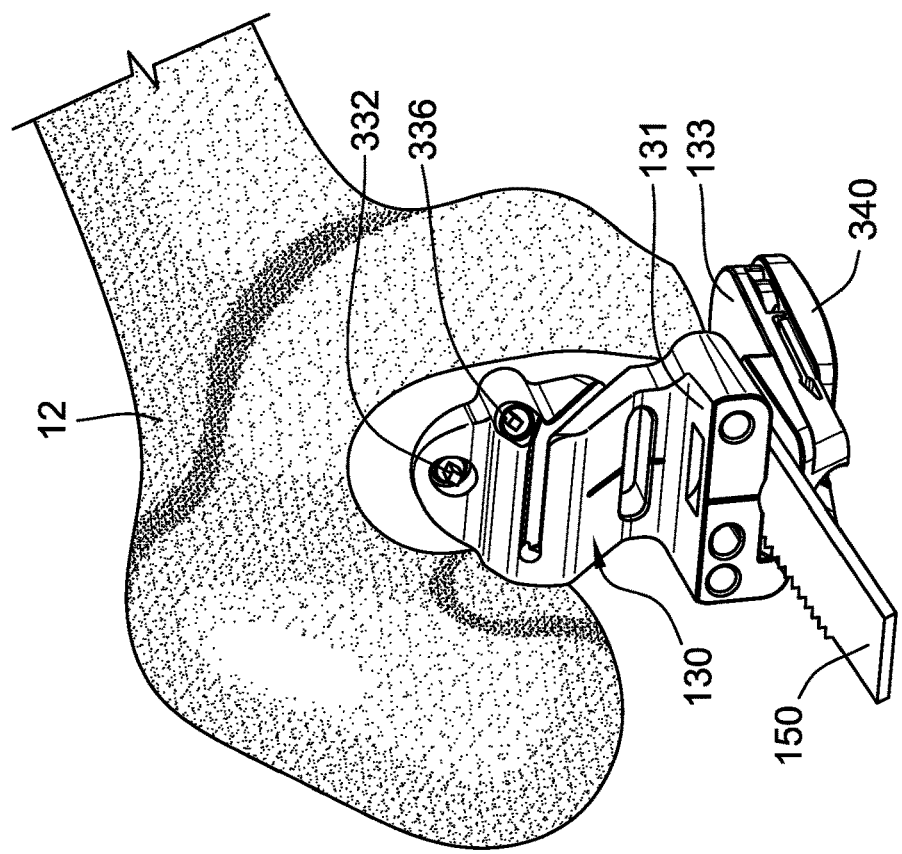
FIG. 33D illustrates the use of the femoral preparation guide of FIG. 13 in creating the posterior resection in more detail.

FIGS. 33D and 33E illustrate that the flat posterior surface 152 from the saw 150 produces a clearance region to permit the saw 160 to create the chamfer surface 162. By first developing the flat posterior surface 152, the saw 160 is required to cut less bone and does not need to be inserted as deep, thereby minimizing the chance for the saw 160 to bottom-out on the lower skid 133 on the posterior region of the femoral preparation guide 130.

FIG. 33E also illustrates the slot 339 on the posterior skid 133 of the femoral preparation guide 130 that is used for attachment of the selected shim 340 to the femoral preparation guide 130. In one embodiment of the invention, the femoral preparation guide 130 includes the slot 339 (or other attachment features) to receive corresponding mating protrusions on the curved spacer shims 340 in the sagittal plane. The spacer shims 340 may be locked into the femoral preparation guide 130 through a dovetail-mating connection in which the selected shim 340 has a dovetail-shaped protrusion 342 (shown in FIG. 34B) that is slid into a corresponding dovetail slot 339 in the lower skid 133. The lower skid 133 may also include a leaf spring within the slot 339 to provide a snug interference fit with the selected shim 340 as it is slid into place. Alternatively, the spacer shims 340 may be locked into the femoral preparation guide 130 through a rotating motion, e.g., with a bayonet-key connection.

Figure 34A:
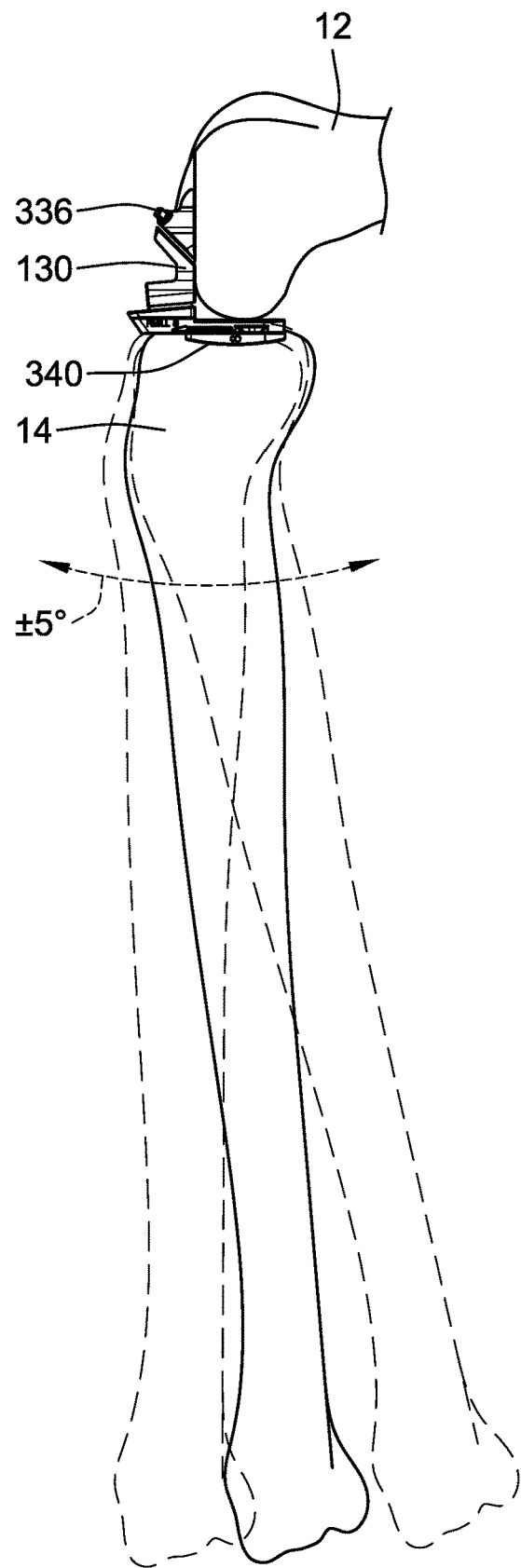
FIG. 34A illustrates details of the femoral preparation guide of FIG. 13 to create the proper spacing relative to the tibial plateau.
Figure 34B:
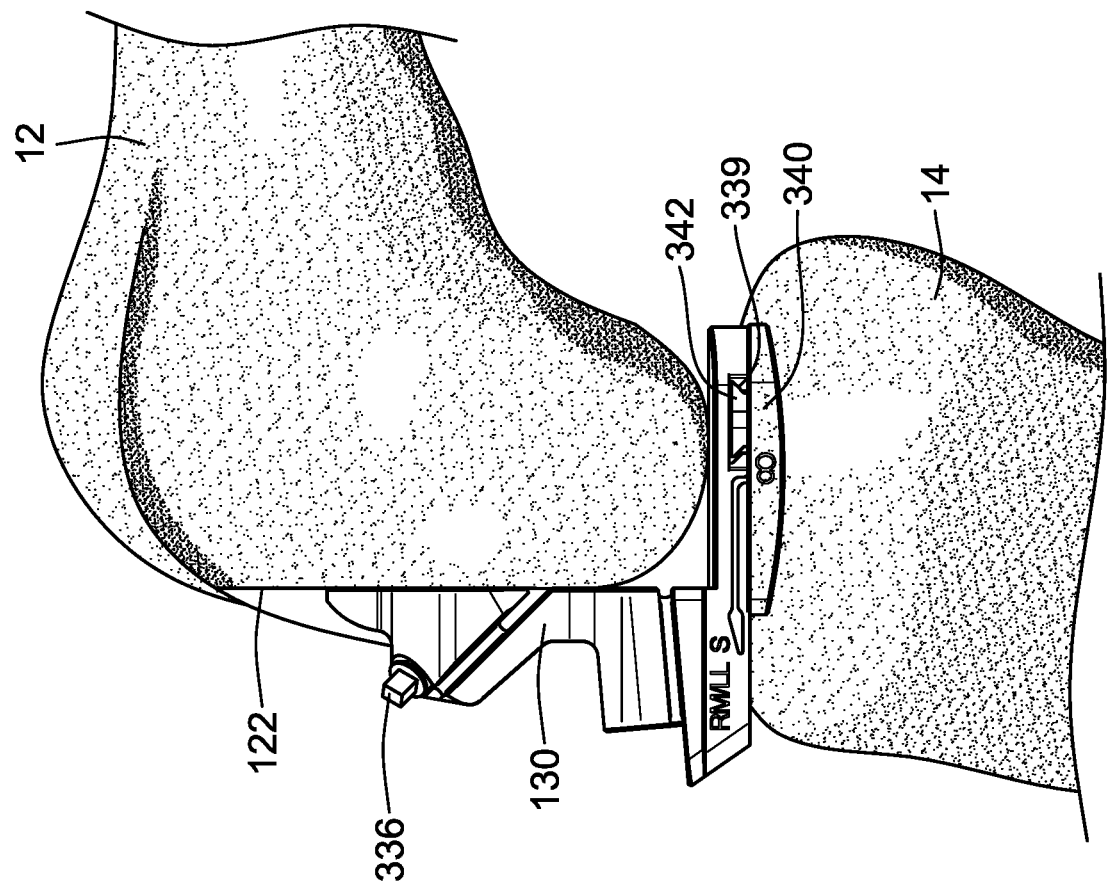
FIG. 34B illustrates more details of the femoral preparation guide of FIG. 13 to create the proper spacing relative to the tibial plateau.

FIGS. 34A and 34B illustrate the functionality of the femoral preparation guide 130 to create the proper spacing relative to the tibial plateau. The curved spacer shims 340 are available in multiple sizes (e.g., thickness and curvature) to adequately fill the joint space. In one preferred embodiment, the flexion space should be about 10 mm. However, in some cases the flexion space may be tighter due to a restricted flexion (e.g., 8-9 mm) or may be looser (e.g., 11-12 mm) due to excessive wear or ligament instability. The curvature of the spacer shims 340 mimics the typical radii of the posterior femoral condyle. This curvature allows for some tibio-femoral movement (i.e., slight flexion), whereas a rectangular shaped spacer would rigidly fix the tibio-femoral position at 90 to 95 degrees (depending on tibial slope). In one preferred embodiment, the combined thicknesses of the lower skid 133 and the selected shim 340 corresponds to the combined thicknesses of the tibial baseplate 20 and the tibial insert 30. For example, the lower skid 133 of the femoral preparation guide 130 is about 3 mm in thickness and the spacer shim 340 is about 5 mm in thickness, leading to a combined thickness of about 8 mm. However, that spacer shim 340 may be labeled as an "8 mm shim", knowing that its combined thickness with the lower skid 133 results in a total combined thickness of 8 mm.

The use of spacer shims 340 on the femoral preparation guide 130 with the desired sagittal curvature in FIGS. 34A-34B provides for key advantages to the overall system. First, the curved spacer shims 340 fill the flexion space, resulting in rectangular, balanced space in frontal plane. Second, the curved spacer shims 340 leverage the tension being placed on the ligaments to further stabilize the overall fixation of the femoral positioning guide, providing more accurate and repeatable preparation. Third, the curved spacer shims 340 have a sagittal curved aspect that accommodates subtle movement of the knee (tibio-femoral articulation) during trial runs with these components. That is, tibial motion is within 85-95 degrees during flexion (as shown in FIG. 34A) during the procedure, and prevents loosening of the entire femoral preparation guide 130 from the bone. When assembled to posterior skid 133 of femoral preparation guide 130, the shims 340 and the skid 133 represent the combined thickness of the tibial insert 30 and tibial baseplate 20 (shown in FIGS. 3 and 31). For example, the shims 340 may have result in a combined thickness with the lower skid 133 of about 8, 9, 10, and 12 mm, which matches the available combined thicknesses from the kit of tibial inserts 30 plus the tibial baseplate 20. In other words, the shims 340 are available in various thicknesses that allow them to correspond with the thickness of the selected tibial insert 30.

Alternative Implementations

Alternative Implementation 1. A femoral preparation guide for use on a condyle of a femur during a surgical procedure, the condyle for receiving a femoral condylar implant, the femoral preparation guide comprising: a posterior portion for fitting over a posterior region of the condyle; a distal portion for fitting over a distal region of the condyle, the distal portion being at an angle relative to the posterior portion; and first and second resections slots on the distal portion for receiving cutting tools that provide two resections of the condyle, the first and second resections slots being at angles relative to each other.

Alternative Implementation 2. The femoral preparation guide of Alternative Implementation 1, wherein the first resection slot is for creating a first posterior cut in the condyle and the second resection slot is for creating a second posterior cut in the condyle, the second posterior cut providing a chamfer cut that is at an angle relative to the first posterior cut.

Alternative Implementation 3. The femoral preparation guide of Alternative Implementation 2, wherein the first posterior cut provides clearance for creating the second posterior cut.

Alternative Implementation 4. The femoral preparation guide of Alternative Implementation 1, further including a guide hole for creating a posterior hole that receives a portion of the femoral condylar implant.

Alternative Implementation 5. The femoral preparation guide of Alternative Implementation 1, wherein the distal portion has a flat surface for engaging a flat resected surface on the condyle.

Alternative Implementation 6. The femoral preparation guide of Alternative Implementation 1, wherein the distal portion and posterior portion define a periphery, at least a portion of the periphery substantially matching a portion of an implant periphery of the femoral condylar implant to provide an indication of a position of the femoral condylar implant when the femoral condylar implant is subsequently installed on the condyle.

Alternative Implementation 7. The femoral preparation guide of Alternative Implementation 1, wherein the posterior portion includes a region to receive a shim that provides guidance for a measurement of the joint space to the tibia.

Alternative Implementation 8. The femoral preparation guide of Alternative Implementation 7, wherein the shim is selected from one of a plurality of shims of different sizes.

Alternative Implementation 9. The femoral preparation guide of Alternative Implementation 1, wherein the distal portion includes a plurality of guide holes for receiving pins, the guide holes being at different angles relative to each other.

Alternative Implementation 10. The femoral preparation guide of Alternative Implementation 1, wherein the femoral preparation guide is part of a kit of femoral preparation guides, each femoral preparation guide within the kit corresponding to a certain size of femoral condylar implant.

Alternative Implementation 11. A femoral preparation guide for use on a condyle of a femur during a surgical procedure, the condyle for receiving a femoral condylar implant, the femoral preparation guide comprising: a posterior portion for fitting over a posterior region of the condyle; a distal portion for fitting over a distal region of the condyle, the distal portion being at an angle relative to the posterior portion; and wherein the distal portion and posterior portion define a periphery, at least a portion of the periphery substantially matching a portion of an implant periphery of the femoral condylar implant for providing an indication of a position of the femoral condylar implant on the condyle when the femoral condylar implant is subsequently installed on the condyle.

Alternative Implementation 12. The femoral preparation guide of Alternative Implementation 11, further including first and second resections slots on the distal portion for receiving cutting tools that provide two resections of the condyle, the first and second resections slots being at angles relative to each other.

Alternative Implementation 13. The femoral preparation guide of Alternative Implementation 12, wherein the first resection slot is for creating a first posterior cut in the condyle and the second resection slot is for creating a second posterior cut in the condyle, the second posterior cut providing a chamfer cut that is at an angle relative to the first posterior cut.

Alternative Implementation 14. The femoral preparation guide of Alternative Implementation 13, wherein the first posterior cut provides clearance for creating the second posterior cut.

Alternative Implementation 15. The femoral preparation guide of Alternative Implementation 11, further including a guide hole for creating a posterior hole that receives a portion of the femoral condylar implant.

Alternative Implementation 16. The femoral preparation guide of Alternative Implementation 11, wherein the distal portion has a flat surface for engaging a flat resected surface on the condyle.

Alternative Implementation 17. The femoral preparation guide of Alternative Implementation 11, wherein the posterior portion includes a region to receive a shim that provides guidance for a measurement of the joint space to the tibia.

Alternative Implementation 18. The femoral preparation guide of Alternative Implementation 17, wherein the shim is selected from one of a plurality of shims of different sizes.

Alternative Implementation 19. The femoral preparation guide of Alternative Implementation 11, wherein the distal portion includes a plurality of guide holes for receiving pins, the guide holes being at different angles relative to each other.

Alternative Implementation 20. The femoral preparation guide of Alternative Implementation 11, wherein the femoral preparation guide is part of a kit of femoral preparation guides, each femoral preparation guide within the kit corresponding to a certain size of femoral condylar implant.

Alternative Implementation 21. A femoral preparation guide for use on a condyle of a femur during a surgical procedure, the condyle for receiving a femoral condylar implant, the femoral preparation guide comprising: a posterior portion for fitting over a posterior region of the condyle; a distal portion for fitting over a distal region of the condyle, the distal portion being at an angle relative to the posterior portion; a chamfer resection slot on the distal portion for receiving a cutting tool that provides a chamfer surface on the condyle that is angled relative to both the posterior and distal portions; and a guide hole for receiving a drill that creates a peg hole that is located on the chamfer surface of the condyle.

Alternative Implementation 22. The femoral preparation guide of Alternative Implementation 21, further including a posterior resection slot on the distal portion for receiving a cutting tool providing a posterior resection of the condyle, the posterior resection slot being at an angle relative to the chamfer resection slot.

Alternative Implementation 23. The femoral preparation guide of Alternative Implementation 22, wherein the posterior resection slot provides a cut that provides clearance for the cutting tool that provides a chamfer surface.

Alternative Implementation 24. The femoral preparation guide of Alternative Implementation 21, wherein the distal portion and posterior portion define a periphery, at least a portion of the periphery substantially matching a portion of an implant periphery of the femoral condylar implant for providing an indication of a position of the femoral condylar implant on the condyle when the femoral condylar implant is subsequently installed on the condyle.

Alternative Implementation 25. The femoral preparation guide of Alternative Implementation 21, wherein the distal portion has a flat surface for engaging a flat resected surface on the condyle.

Alternative Implementation 26. The femoral preparation guide of Alternative Implementation 21, wherein the posterior portion includes a region to receive a shim that provides guidance for a measurement of the joint space between the femur and a corresponding tibia.

Alternative Implementation 27. The femoral preparation guide of Alternative Implementation 26, wherein the shim is selected from one of a plurality of shims of different sizes.

Alternative Implementation 28. The femoral preparation guide of Alternative Implementation 21, wherein the distal portion includes a plurality of guide holes for receiving pins, the guide holes being at different angles relative to each other.

Alternative Implementation 29. The femoral preparation guide of Alternative Implementation 21, wherein the femoral preparation guide is part of a kit of femoral preparation guides, each femoral preparation guide within the kit corresponding to a certain size of femoral condylar implant.

Alternative Implementation 30. A femoral preparation guide for use on a condyle of a femur during a surgical procedure, the condyle for receiving a femoral condylar implant, the femoral preparation guide comprising: a posterior portion for fitting over a posterior region of the condyle, the posterior portion having an attachment element on an underside surface of the posterior portion; a distal portion for fitting over a distal region of the condyle; and a shim coupled to the attachment element for providing an appropriate joint space to the tibia, the shim being selected from a plurality of shims, the plurality of shims being of different sizes.

Alternative Implementation 31. The femoral preparation guide of Alternative Implementation 30, wherein the shim and attachment element include dovetail mating portions.

Alternative Implementation 32. The femoral preparation guide of Alternative Implementation 30, wherein the shim and attachment element are coupled via a rotation movement that engages mating features.

Alternative Implementation 33. The femoral preparation guide of Alternative Implementation 32, wherein the mating features are bayonet-key mating portions.

Alternative Implementation 34. The femoral preparation guide of Alternative Implementation 30, wherein the shim includes a curved sagittal surface that mimics a radius of a posterior region of the condyle.

Alternative Implementation 35. A femoral preparation guide for use on a condyle of a femur during a surgical procedure, the condyle for receiving a femoral condylar implant, the femoral preparation guide comprising: a main body for fitting over the condyle, the main body having one or more slots for guiding one or more resection cuts of the condyle, the main body having a periphery, at least a portion of the periphery substantially matching a portion of an implant periphery of the femoral condylar implant for providing an indication of (i) a medial-lateral position of the femoral condylar implant that is subsequently installed on the condyle, (ii) a size of the femoral condylar implant that is subsequently installed on the condyle, or (iii) both (i) and (ii).

Alternative Implementation 36. The femoral preparation guide of Alternative Implementation 35, having features and/or functionality in accordance with any of Alternative Implementation 1 to 34.

Alternative Implementation 37. A system including one more femoral preparation components for use on a condyle of a femur during a surgical procedure, the condyle for receiving a femoral condylar implant, the system comprising: a femoral preparation guide having (i) a posterior portion for fitting over a posterior region of the condyle, (ii) a distal portion for fitting over a distal region of the condyle, (iii) at least one resection slot for receiving a cutting tool that provides a resection of the condyle, and (iv) a first guide hole for receiving a drill that creates a first peg hole that is located on the condyle; and a femoral trial guide for placement over the condyle after the resection developed with the femoral preparation guide, the femoral trial guide including a second guide hole for receiving a drill that creates a second peg hole that is located on the condyle, the first and second peg holes for receiving pegs on the femoral condylar implant.

Alternative Implementation 38. The femoral preparation components of Alternative Implementation 37, having features and/or functionality in accordance with any of Alternative Implementation 1 to 34.

Alternative Implementation 39. A system including one more femoral preparation components for use on a condyle of a femur during a surgical procedure, the condyle for receiving a femoral condylar implant, the system comprising: a femoral resection guide block that slides over a spacer component positioned in region below the condyle, the femoral resection guide block including a resection slot for receiving a cutting tool that provides a first resection of the condyle; a femoral preparation guide for attachment to the condyle in the region of the first resection, the femoral preparation guide having two resection slots for receiving cutting tools that provide a second resection and a third resection of the condyle, the femoral preparation guide including a first guide hole for receiving a drill that creates a first peg hole that is located on the condyle; and a femoral trial guide for placement over the condyle after the resections developed with the femoral preparation guide, the femoral trial guide including a second guide hole for receiving a drill that creates a second peg hole that is located on the condyle.

Alternative Implementation 40. The femoral preparation components of Alternative Implementation 39, having features and/or functionality in accordance with any of Alternative Implementation 1 to 34.

Alternative Implementation 41. A femoral trial guide for use on a condyle of a femur during a surgical procedure, the condyle for receiving a femoral condylar implant, the femoral trial guide comprising: a curved outer surface to replicate an outer surface of the femoral condylar implant for providing an indication of the position and movement of femoral condylar implant that is subsequently implanted; and a guide hole for receiving a drill that creates a peg hole that is located on the condyle.

Alternative Implementation 42. A method of preparing a condyle for receiving a femoral condylar implant using one or more of the components set forth in any of Alternative Implementation 1 to 41.

Alternative Implementation 43. A kit of components for preparing the femur and the tibia for partial knee replacement, the kit including a tibial surgical template, a tibial trial insert that mates the tibial surgical template, and one or more of the components set forth in any of Alternative Implementation 1 to 41.

Alternative Implementation 44. A kit of components for preparing the tibia for partial knee replacement, the kit including one or more of the tibial-related components described relative to any of FIGS. 5, 6, 7, 20-26.

One or more elements or aspects or steps, or any portion(s) thereof, from one or more of any of Alternative Implementations 1 to 44 above can be combined with one or more elements or aspects or steps, or any portion(s) thereof, from one or more of any of the other Alternative Implementations 1 to 44 or combinations thereof, to form one or more additional implementations and/or claims of the present disclosure.

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

What is claimed is:

1. A femoral preparation guide for use on a condyle of a femur during a surgical procedure, the condyle for receiving a femoral condylar implant, the femoral preparation guide comprising:
   a posterior portion for fitting over a posterior region of the condyle, the posterior portion including a lower skid and a template bore, wherein the lower skid comprises a first side that faces the posterior region of the condyle when the posterior portion is fitted over the posterior region of the condyle and a second side that faces away from the posterior region of the condyle when the posterior portion is fitted over the posterior region of the condyle, and wherein the template bore defines a generally cylindrical opening disposed through a first resection slot;
   a distal portion for fitting over a distal region of the condyle, the distal portion being at an angle relative to the posterior portion and including a first through-bore and a second through-bore, wherein a central axis of the first through-bore is oriented to be non-parallel with respect to a central axis of the second through-bore, wherein the distal portion has an inside surface that faces the distal region of the condyle when the distal portion is fitted over the distal region of the condyle, wherein the inside surface and the first side intersect along a line, wherein the second side has a slot oriented to be parallel to the line, the slot having a dovetail cross-section;
   the first resection slot and a second resection slot disposed through the distal portion for receiving cutting tools that provide two resections of the condyle; and
   a shim of a plurality of shims, the shim having a flat surface and a protrusion having a dovetail cross-section extending from the flat surface on a first side of the shim, and a convex curved surface on a second side of the shim opposite to the first side, wherein a cross-section of the convex curved surface is disposed parallel to the cross-section of the dovetail protrusion, the shim removably attachable to the second side of the lower skid by the protrusion sliding into the slot having the dovetail cross-section;
   wherein the shim is sized so that when the shim is removably attached to the second side of the lower skid the shim provides a measure of spacing between the posterior portion and a resected end of a tibia; and
   wherein the convex curved surface is shaped so that when the shim is removably attached to the second side of the lower skid, the convex curved surface accommodates movement of the tibia in flexion relative to the femur.

2. The femoral preparation guide of claim 1, wherein the first resection slot is for creating a first posterior cut in the condyle and the second resection slot is for creating a second posterior cut in the condyle, the second posterior cut providing a chamfer cut that is at an angle relative to the first posterior cut, and wherein the first posterior cut provides clearance for creating the second posterior cut.

3. The femoral preparation guide of claim 1, wherein the distal portion and posterior portion define a periphery, at least a portion of the periphery substantially matching a portion of an implant periphery of the femoral condylar implant to provide an indication of a position of the femoral condylar implant when the femoral condylar implant is subsequently installed on the condyle.

4. The femoral preparation guide of claim 1, wherein the first through-bore and the second through-bore are guide holes for receiving pins.

5. The femoral preparation guide of claim 1, wherein each shim of the plurality of shims has a different size measured between the flat surface and the convex curved surface.

6. The femoral preparation guide of claim 1, wherein the convex curved surface of the shim is configured to mimic a radius of a posterior region of the condyle.

7. A femoral preparation guide for use on a condyle of a femur during a surgical procedure, the condyle for receiving a femoral condylar implant, the femoral preparation guide comprising:
   a posterior portion for fitting over a posterior region of the condyle, the posterior portion including a lower skid and a template bore, wherein the lower skid comprises a first side that faces the posterior region of the condyle when the posterior portion is fitted over the posterior region of the condyle and a second side that faces away from the posterior region of the condyle when the posterior portion is fitted over the posterior region of the condyle, and wherein the template bore defines a generally cylindrical opening disposed through a first resection slot; and a distal portion for fitting over a distal region of the condyle, the distal portion being at an angle relative to the posterior portion, the distal portion and posterior portion defining a periphery, at least a portion of the periphery substantially matching a portion of an implant periphery of the femoral condylar implant for providing an indication of a position of the femoral condylar implant on the condyle when the femoral condylar implant is subsequently installed on the condyle, wherein the distal portion includes a first through-bore and a second through-bore, wherein a central axis of the first through-bore is oriented to be non-parallel with respect to a central axis of the second through-bore, wherein the distal portion has an inside surface that faces the distal region of the condyle when the distal portion is fitted over the distal region of the condyle, wherein the inside surface and the first side intersect along a line, wherein the second side has a slot oriented to be parallel to the line, the slot having a dovetail cross-section;

the first resection slot and a second resection slot disposed through the distal portion for receiving cutting tools that provide two resections of the condyle; and a shim of a plurality of shims, the shim having a flat surface and a protrusion having a dovetail cross-section extending from the flat surface on a first side of the shim, and a convex curved surface on a second side of the shim opposite to the first side, wherein a cross-section of the convex curved surface is disposed parallel to the cross-section of the dovetail protrusion, the shim removably attachable to the second side of the lower skid by the protrusion sliding into the slot having the dovetail cross-section;

wherein the shim is sized so that when the shim is removably attached to the second side of the lower skid the shim provides a measure of spacing between the posterior portion and a resected end of a tibia; and wherein the convex curved surface is shaped so that when the shim is removably attached to the second side of the lower skid, the convex curved surface accommodates movement of the tibia in flexion relative to the femur.

8. The femoral preparation guide of claim 7, the second posterior cut providing a chamfer cut that is at an angle relative to the first posterior cut, and wherein the first posterior cut provides clearance for creating the second posterior cut.

9. The femoral preparation guide of claim 7, further including a guide hole for creating a posterior hole that receives a portion of the femoral condylar implant.

10. The femoral preparation guide of claim 7, wherein each shim of the plurality of shims has a different size measured between the flat surface and the convex curved surface.

11. The femoral preparation guide of claim 7, wherein the first through-bore and the second through-bore are guide holes for receiving pins.

12. A femoral preparation guide for use on a condyle of a femur during a surgical procedure, the condyle for receiving a femoral condylar implant, the femoral preparation guide comprising:

a posterior portion for fitting over a posterior region of the condyle, the posterior portion including a lower skid and a template bore, wherein the lower skid comprises a first side that faces the posterior region of the condyle when the posterior portion is fitted over the posterior region of the condyle and a second side that faces away from the posterior region of the condyle when the posterior portion is fitted over the posterior region of the condyle, and wherein the template bore defines a generally cylindrical opening disposed through a posterior resection slot;

a distal portion for fitting over a distal region of the condyle, the distal portion being at an angle relative to the posterior portion and including a first through-bore and a second through-bore, wherein a central axis of the first through-bore is oriented to be non-parallel with respect to a central axis of the second through-bore, wherein the distal portion has an inside surface that faces the distal region of the condyle when the distal portion is fitted over the distal region of the condyle, wherein the inside surface and the first side intersect along a line, wherein the second side has a slot oriented to be parallel to the line, the slot having a dovetail cross-section;

a chamfer resection slot on the distal portion for receiving a first cutting tool that provides a chamfer surface on the condyle;

the posterior resection slot on the distal portion for receiving a second cutting tool; and a shim of a plurality of shims, the shim having a flat surface and a protrusion having a dovetail cross-section extending from the flat surface on a first side of the shim, and a convex curved surface on a second side of the shim opposite to the first side, wherein a cross-section of the convex curved surface is disposed parallel to the cross-section of the dovetail protrusion, the shim removably attachable to the second side of the lower skid by the protrusion sliding into the slot having the dovetail cross-section;

wherein the shim is sized so that when the shim is removably attached to the second side of the lower skid the shim provides a measure of spacing between the posterior portion and a resected end of a tibia; and wherein the convex curved surface is shaped so that when the shim is removably attached to the second side of the lower skid, the convex curved surface accommodates movement of the tibia in flexion relative to the femur.

13. The femoral preparation guide of claim 12, wherein the distal portion and posterior portion define a periphery, at least a portion of the periphery substantially matching a portion of an implant periphery of the femoral condylar implant for providing an indication of a position of the femoral condylar implant on the condyle when the femoral condylar implant is subsequently installed on the condyle.

14. The femoral preparation guide of claim 12, wherein the inside surface has a flat surface for engaging a flat resected surface on the condyle.

15. The femoral preparation guide of claim 12, wherein the first through-bore and the second through-bore are guide holes for receiving pins.

* * * * *